United States Patent
De Sio et al.

(10) Patent No.: US 9,823,490 B2
(45) Date of Patent: *Nov. 21, 2017

(54) METHODS AND APPARATUS FOR OPHTHALMIC DEVICES INCLUDING CYCLOIDALLY ORIENTED LIQUID CRYSTAL LAYERS

(71) Applicant: Johnson & Johnson Vision Care, Inc., Jacksonville, FL (US)

(72) Inventors: Luciano De Sio, Winter Park, FL (US); Frederick A. Flitsch, New Windsor, NY (US); Praveen Pandojirao-S, Jacksonville, FL (US); Randall Braxton Pugh, Jacksonville, FL (US); Svetlan Serak, Oviedo, FL (US); Nelson V. Tabirian, Winter Park, FL (US); Adam Toner, Jacksonville, FL (US); Olena Uskova, Winter Park, FL (US); James Daniel Riall, St. Johns, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/165,098

(22) Filed: May 26, 2016

(65) Prior Publication Data
US 2016/0270909 A1 Sep. 22, 2016

Related U.S. Application Data

(62) Division of application No. 14/487,888, filed on Sep. 16, 2014, now Pat. No. 9,541,772.
(Continued)

(51) Int. Cl.
*A61F 2/16* (2006.01)
*G02C 7/04* (2006.01)
(Continued)

(52) U.S. Cl.
CPC ............. *G02C 7/04* (2013.01); *A61F 2/1624* (2013.01); *A61F 2/1627* (2013.01);
(Continued)

(58) Field of Classification Search
CPC ...... A61F 2002/1696; A61F 2210/0076; A61F 2/1624; A61F 2/1627; A61F 2/1648;
(Continued)

(56) References Cited

U.S. PATENT DOCUMENTS

| 5,682,210 A | 10/1997 | Weirich |
| 6,120,460 A | 9/2000 | Abreu |

(Continued)

FOREIGN PATENT DOCUMENTS

| EP | 1947501 A2 | 7/2008 |
| EP | 2063311 A1 | 5/2009 |

(Continued)

OTHER PUBLICATIONS

Serak, S.V., Polarization-controlled switching in cycloidal nematic liquid crystals, Optical Society of America, Oct. 10, 2006.
(Continued)

*Primary Examiner* — David H Willse
*Assistant Examiner* — Tiffany Shipmon

(57) ABSTRACT

This invention discloses methods and apparatus for providing a variable optic insert into an ophthalmic lens. A liquid crystal layer may be used to provide a variable optic function and in some examples, an alignment layer for the liquid crystal layer may be patterned in a cycloidally dependent manner. The patterning may allow for a polarization dependent lens in some examples. An energy source is capable of powering the variable optic insert included within the ophthalmic lens. In some examples, an ophthalmic lens is cast-molded from a silicone hydrogel. The various ophthal-
(Continued)

mic lens entities may include electroactive liquid crystal layers to electrically control optical characteristics.

1 Claim, 17 Drawing Sheets

Related U.S. Application Data

(60) Provisional application No. 61/878,723, filed on Sep. 17, 2013.

(51) Int. Cl.
- G02C 7/08 (2006.01)
- G02C 7/12 (2006.01)
- G02C 7/10 (2006.01)

(52) U.S. Cl.
CPC ............ A61F 2/1648 (2013.01); G02C 7/041 (2013.01); G02C 7/049 (2013.01); G02C 7/083 (2013.01); G02C 7/12 (2013.01); A61F 2002/1696 (2015.04); A61F 2210/0076 (2013.01); G02C 7/101 (2013.01); G02C 2202/16 (2013.01); G02C 2202/18 (2013.01)

(58) Field of Classification Search
CPC ........ G02C 7/041; G02C 7/049; G02C 7/083; G02C 7/12; G02C 7/101; G02C 2202/16; G02C 2202/18; B29D 11/00817; B29D 11/00826
USPC ........................................................ 623/6.22
See application file for complete search history.

(56) References Cited

U.S. PATENT DOCUMENTS

| | | | |
|---|---|---|---|
| 6,312,393 | B1 | 11/2001 | Abreu |
| 6,364,482 | B1 | 4/2002 | Roffman |
| 6,364,483 | B1 | 4/2002 | Grossinger |
| 6,570,386 | B2 | 5/2003 | Goldstein |
| 6,864,951 | B1 | 3/2005 | Ren et al. |
| 7,018,040 | B2 | 3/2006 | Blum |
| 7,169,106 | B2 | 1/2007 | Fleischman |
| 7,626,562 | B2 | 12/2009 | Iwasaki |
| 7,708,401 | B2 | 5/2010 | Sabeta |
| 7,931,832 | B2 | 4/2011 | Pugh |
| 8,047,651 | B2 | 11/2011 | Blum |
| 8,602,560 | B2 | 12/2013 | Marin |
| 8,906,088 | B2 | 12/2014 | Pugh |
| 2004/0021929 | A1 | 2/2004 | Nishioka |
| 2004/0027536 | A1 | 2/2004 | Blum |
| 2005/0003107 | A1 | 1/2005 | Kumar |
| 2005/0062679 | A1 | 3/2005 | Aharoni |
| 2005/0140924 | A1 | 6/2005 | Blum et al. |
| 2005/0151926 | A1 | 7/2005 | Kumar |
| 2006/0164593 | A1 | 7/2006 | Peyghambarian |
| 2006/0209238 | A1 | 9/2006 | Shiraogawa |
| 2008/0208335 | A1 | 8/2008 | Blum |
| 2008/0278675 | A1 | 11/2008 | Escuti |
| 2009/0033863 | A1* | 2/2009 | Blum ........................ A61F 2/14 351/159.34 |
| 2009/0076367 | A1 | 3/2009 | Sit |
| 2009/0096981 | A1 | 4/2009 | Clarke |
| 2009/0279050 | A1 | 11/2009 | McGinn et al. |
| 2009/0316097 | A1 | 12/2009 | Presniakov |
| 2010/0001926 | A1 | 1/2010 | Amirparviz |
| 2010/0079724 | A1 | 4/2010 | Pugh |
| 2010/0103368 | A1 | 4/2010 | Amirparviz |
| 2010/0103369 | A1 | 4/2010 | Pugh |
| 2010/0302490 | A1 | 12/2010 | Chiu |
| 2011/0028807 | A1 | 2/2011 | Abreu |
| 2011/0184271 | A1 | 7/2011 | Veciana |
| 2011/0188120 | A1 | 8/2011 | Tabirian |
| 2011/0262844 | A1 | 10/2011 | Tabirian |
| 2011/0292306 | A1 | 12/2011 | Kim |
| 2012/0140167 | A1 | 6/2012 | Blum |
| 2012/0188467 | A1 | 7/2012 | Escuti |
| 2012/0212696 | A1 | 8/2012 | Trajkovska |
| 2012/0218483 | A1 | 8/2012 | Archambeau et al. |
| 2012/0224127 | A1 | 9/2012 | Kwok |
| 2012/0229754 | A1 | 9/2012 | Iyer |
| 2013/0050639 | A1 | 2/2013 | Trajkovska |
| 2013/0077013 | A1 | 3/2013 | Yamazaki |
| 2013/0166025 | A1 | 6/2013 | Pugh |
| 2013/0208347 | A1 | 8/2013 | Haddock |
| 2013/0245754 | A1 | 9/2013 | Blum |
| 2014/0036172 | A1 | 2/2014 | Trajkovska-Broach |
| 2014/0132904 | A1 | 5/2014 | Bos |
| 2014/0327875 | A1 | 11/2014 | Blum |
| 2015/0077662 | A1 | 3/2015 | Pugh |
| 2015/0138454 | A1 | 5/2015 | Pugh |

FOREIGN PATENT DOCUMENTS

| | | |
|---|---|---|
| EP | 2431790 A1 | 3/2012 |
| EP | 2602657 A1 | 6/2013 |
| GB | 2493627 A | 2/2013 |
| JP | 11352445 A | 12/1999 |
| TW | 200848001 A | 12/2008 |
| TW | 201026489 A | 7/2010 |
| WO | WO2000049452 A1 | 8/2000 |
| WO | WO2001002895 A1 | 1/2001 |
| WO | WO2002057836 A1 | 7/2002 |
| WO | WO2004015460 A2 | 2/2004 |
| WO | WO2005006035 A1 | 1/2005 |
| WO | WO2006078806 A2 | 7/2006 |
| WO | WO2008091859 A1 | 7/2008 |
| WO | WO2009048647 A1 | 4/2009 |
| WO | WO2011026315 A1 | 3/2011 |
| WO | WO2012103497 A1 | 8/2012 |
| WO | WO2012122411 A1 | 9/2012 |
| WO | WO2012170066 A1 | 12/2012 |
| WO | WO2013096781 A1 | 6/2013 |
| WO | WO2013113278 A1 | 8/2013 |

OTHER PUBLICATIONS

Milton, Harry E. et al., "Electronic Liquid Crystal Contact Lenses for the Correction of Presbyopia", Optics Express, Apr. 7, 2014, vol. 22, No. 7.
Chen,Yuan et al., "High Performance Negative Dielectric Anistrophy Liquid Crystals for Display Applications", Crystals, 2013, 3, 483-503.
Syed, Ishtiaque M. et al., "Novel Switching Mode in a Vertically Aligned Liquid Crystal Contact Lens", Optics Express, Apr. 20, 2015, vol. 23, No. 8.
Ren Hongwen et al., "Tunable Fresnel Lens Using Nanoscale Polymer-Dispersed Liquid Crystals", Applied Physics Letters, American Institute of Physics, vol. 83, No. 8, Aug. 25, 2003, pp. 1515-1517.
Nersisyan S. R. et al., "The Principals of Laser Beam Control with Polarization Gratings Introduced as Diifractive Waeplates", Proceedings of Spie, SPIE International Society for Optical Engineering, vol. 7775, Aug. 1, 2010, pp. 77750.
L. Marrucci, et al., "Pancharatnam-Berry phase optical elements for wave front shaping in the visible domain: Switchable helical mode generation", Applied Physics Letters 88, 221102-1, 2006.
Ervin Goldfain, "exact Raytracing Formulae for Parabolic Axial Grin Lenses", Gradient Index, Miniature, and Diifractive Optical Systems, vol. 3778, pp. 2-10.
Asatryan, K., et al., "Optical Lens with Electrically Variable Focus Using an Optically Hidden Dielectric Structure", Optics Express, vol. 18, No. 13, pp. 13981-13992 (2010).
Hoogboom, J., et al., "LCD Alignment Layers, Controlling Nematic Domain Properties", Journal of Material Chemistry, vol. 16, pp. 1305-1314 (2006).
Laude, Vincent, "Twisted-Nematic Liquid-Crystal Pixelatd Active Lens", Optics Communications, vol. 153, pp. 134-152 (1998).

(56) References Cited

OTHER PUBLICATIONS

Birefringence in Liquid Crystals, http://plc.cwru.edu/tutorial/enhanced/files/lc/biref.htm, pp. 1-4 Dec. 10, 2012.
De Smet, J. et al., "Design and Wrinkling Behavior of a Contact Lens with an Integrated Liquid Crystal Light Modulator", Journal of Display Technology, May 31, 2012, vol. 8, No. 5, pp. 229-305.
Ren, H. et al., "Tunable-Focus Microlens Arrays using Nanosized Polymer-Dispered Liquid Crystal Droplets", Optics Communications, Mar. 1, 2005, vol. 247, No. 1-3, pp. 101-106.

* cited by examiner

METHODS AND APPARATUS FOR OPHTHALMIC DEVICES INCLUDING CYCLOIDALLY ORIENTED LIQUID CRYSTAL LAYERS

CROSS REFERENCE TO RELATED APPLICATIONS

This application is a divisional of U.S. patent application Ser. No. 14/487,888 filed Sep. 16, 2014 which claims the benefit of Provisional Application No. 61/878,723 filed Sep. 17, 2013.

BACKGROUND OF THE INVENTION

1. Field of the Invention

This invention describes an ophthalmic lens device with a variable optic capability and, more specifically, in some examples, the fabrication of an ophthalmic lens with a variable optic insert utilizing liquid crystal elements.

2. Discussion of the Related Art

Traditionally an ophthalmic lens, such as a contact lens or an intraocular lens provided a predetermined optical quality. A contact lens, for example, may provide one or more of the following: vision correcting functionality; cosmetic enhancement; and therapeutic effects, but only a set of vision correction functions. Each function is provided by a physical characteristic of the lens. Basically, a design incorporating a refractive quality into a lens provides vision corrective functionality. A pigment incorporated into the lens may provide a cosmetic enhancement. An active agent incorporated into a lens may provide a diagnostic and/or therapeutic functionality.

To date optical quality in an ophthalmic lens has been designed into the physical characteristic of the lens. Generally, an optical design has been determined and then imparted into the lens during fabrication of the lens, such as, for example through cast molding, or lathing. The optical qualities of the lens have remained static once the lens has been formed. However, wearers may at times find it beneficial to have more than one focal power available to them in order to provide sight accommodation. Unlike spectacle wearers, who may change spectacles to change an optical correction, contact wearers or those with intraocular lenses have not been able to change the optical characteristics of their vision correction without significant effort or the complementing of spectacles with contact lenses or intraocular lenses.

SUMMARY OF THE INVENTION

Accordingly, the present invention includes innovations relating to a variable optic insert with liquid crystal elements that may be energized and incorporated into an ophthalmic device, which is capable of changing the optical quality of the device. Examples of such ophthalmic devices may include a contact lens or an intraocular lens. In addition, methods and apparatus for forming an ophthalmic lens with a variable optic insert with liquid crystal elements are presented. Some examples may also include a cast-molded silicone hydrogel contact lens with a rigid or formable energized insert, which additionally includes a variable optic portion, wherein the insert is included within the ophthalmic lens in a biocompatible fashion. The formable energized insert may also be sandwiched in between independently produced contact lens material such as hydrogel.

The present invention therefore includes disclosure of an ophthalmic lens with a variable optic insert, apparatus for forming an ophthalmic lens with a variable optic insert, and methods for manufacturing the same. An energy source may be deposited or assembled onto a variable optic insert and the insert may be placed in proximity to one, or both of, a first mold part and a second mold part. A composition comprising a reactive monomer mixture (hereafter referred to as a reactive monomer mixture) is placed between the first mold part and the second mold part. The first mold part is positioned proximate to the second mold part thereby forming a lens cavity with the energized media insert and at least some of the reactive monomer mixture in the lens cavity; the reactive monomer mixture is exposed to actinic radiation to form an ophthalmic lens. Lenses are formed via the control of actinic radiation to which the reactive monomer mixture is exposed. In some examples, an ophthalmic lens skirt or an insert-encapsulating layer comprises standard hydrogel ophthalmic lens formulations. Exemplary materials with characteristics that may provide an acceptable match to numerous insert materials may include, for example, the Narafilcon family (including Narafilcon A and Narafilcon B), the Etafilcon family (including Etafilcon A), Galyfilcon A and Senofilcon A.

The methods of forming the variable optic insert with liquid crystal elements and the resulting inserts are important aspects of various examples of the invention. In some examples, the liquid crystal may be located between two alignment layers, which may set the resting orientation for the liquid crystal. In some examples the alignment layers may be patterned in various manners. The patterning of the alignment layers may be performed such that the alignment of the molecules in the alignment layer interacts with liquid crystal molecules to form a smoothly varying cycloidal type pattern from a first orientation in the center of the lens to a second orientation further along a radial axis, where this pattern repeats. In some examples, the period of the repeating pattern may be modulated for various purposes such a contracting the pattern along the axial direction in a second order or parabolic manner. Other contractions or expansions of different orders of the radial dimension may be possible. The smoothly varying pattern may be classified as a cycloidal pattern and since the orientation of liquid crystal molecules may be varied in the plane of a surface, the effective index of refraction of light progressing through the layer or oriented material may be relatively constant. Nevertheless, the cycloidal pattern of molecules may interact with the light in various manners and in particular may impart differential phase shifts to light of right handed versus left handed circular polarization The alignment layers may be in electrical communication with an energy source through electrodes deposited on substrate layers that contain the variable optic portion. The electrodes may be energized through an intermediate interconnect to an energy source or directly through components embedded in the insert.

The energization of the electrode layers may cause a shift in the liquid crystal from a resting orientation which may be patterned in a cycloidal pattern where the pattern may be called a diffractive waveplate lens pattern to an energized orientation where the cycloidal pattern may be not present. In examples that operate with two levels of energization, on or off, the liquid crystal may only have one energized orientation. The waveplate pattern may be formed into thin layers of liquid crystal material at thicknesses less than the wavelength of visible light.

The resulting alignment and orientation of the molecules may affect light that passes through the liquid crystal layer thereby causing the variation in the variable optic insert. For example, the alignment and orientation may act with refractive or diffractive characteristics upon the incident light. Additionally, the effect may include an alteration of the polarization of the light or impact the phase of light depending on polarization. Some examples may include a variable optic insert wherein energization alters a focal characteristic of the lens.

In some examples, the liquid crystal layer may be formed in a manner wherein a polymerizable mixture comprising liquid crystal molecules is caused to polymerize. The monomer(s) used to form the polymer matrix may itself contain attached liquid crystal portions. By controlling the polymerization and including liquid crystal molecules unattached to the monomer compounds a matrix of cross-linked polymer regions may be formed that encompass regions where the individual liquid crystal molecules are located. In some terminology such a combination of cross-linked polymerized molecules with interstitial included liquid crystal molecules may be call a network arrangement. Alignment layers may guide alignment of the liquid crystal molecules which are attached to monomer such that the network of polymerized material is aligned to the guiding alignment layers. In some examples, there may be a smoothly varying pattern formed by various manners into the alignment layers which may then cause the liquid crystal molecules or networks of liquid crystal material to form cycloidal patterns. The attached liquid crystal molecules are locked into an orientation during the polymerization, however the interstitially located liquid crystal molecules may be free to orient in space. When no external influence is present, the free liquid crystal molecules will have their alignment influenced by the matrix of aligned liquid crystal molecules.

Accordingly, in some examples an ophthalmic device may be formed by the incorporation of a variable optic insert comprising liquid crystal molecules within an ophthalmic device. The variable insert may comprise at least a portion which may be located in the optic zone of the ophthalmic device. The variable insert may comprise a front insert piece and a back insert piece. In some examples, the liquid crystal molecules may be aligned into a pattern across at least a first portion of the variable optic insert that varies with a cycloidal pattern. It may also be represented that the orientation of the principal axes of the index of refraction across at least a first portion of the optic insert may vary with a cycloidal manner. The locations in liquid crystal orientation aligning with a radial axis across at least a first portion of the optic insert may have a parabolic dependence on a radial dimension. The locations of the alignment with a radial axis, may also be termed locations of cycloidal maxima and may be designed such that their location relative to the center of the lens may have a primarily parabolic dependence on the radial distance or radial dimension and in some examples, the location of the cycloidal maxima in the cycloidal pattern may have parabolic and higher order parametric dependence on the radial distance from a center of the optic device.

The front and back insert pieces may have either or both of their surfaces curved in various manners, and in some examples the radius of curvature of a back surface on the front insert piece may be approximately the same as the radius of curvature of the front surface of the back insert piece. In an alternative manner of description, in some examples, the front insert piece may have a surface with a first curvature, and the back insert piece may have a second surface with a second curvature. In some examples the first curvature may be approximately the same as the second curvature. An energy source may be included into the lens and into the insert, and in some examples the energy source may be located wherein at least a portion of the energy source is in the non-optic zone of the device.

In some examples the cycloidally patterned layer comprising liquid crystal material may be capable of causing an optical effect supplementary to the effect of the different radii of insert surfaces. In some examples the cycloidally patterned layer may assume a curved shape.

In some examples the ophthalmic device may be a contact lens. In some examples the ophthalmic device may be an intraocular lens.

In some examples the insert of the ophthalmic device may comprise electrodes made of various materials, including transparent materials such as indium tin oxide (ITO), graphene, and oxides of graphene as non-limiting examples. A first electrode may be located proximate to a back surface of a front curve piece, and a second electrode may be located proximate to a front surface of a back curve piece. When an electric potential is applied across the first and second electrodes, an electric field may be established across a liquid crystal layer located between the electrodes. The application of an electric field across the liquid crystal layer may cause free liquid crystal molecules within the layer to physically align with the electric field. In some examples, the free liquid crystal molecules may be located in interstitial regions within a network of polymer and in some examples the polymer backbone may contain chemically bound liquid crystal molecules which may be aligned during polymerization by alignment layers. When the liquid crystal molecules align with the electric field, the alignment may cause a change in the optical characteristics that a light ray may perceive as it traverses the layer containing liquid crystal molecules and may eliminate the cycloidal patterning. A non-limiting example may be that the index of refraction may be altered by the change in alignment. In some examples, the change in optical characteristics may result in a change in focal characteristics of the lens which contains the layer containing liquid crystal molecules and may cause the elimination of a cycloidal characteristic of the layer.

In some examples, the ophthalmic devices as described may include a processor.

In some examples, the ophthalmic devices as described may include an electrical circuit. The electrical circuit may control or direct electric current to flow within the ophthalmic device. The electrical circuit may control electrical current to flow from an energy source to the first and second electrode elements.

The insert device may comprise more than a front insert piece and a back insert piece in some embodiments. An intermediate piece or pieces may be located between the front insert piece and the back insert piece. In an example, a liquid crystal containing layer may be located between the front insert piece and the intermediate piece. The variable insert may comprise at least a portion which may be located in the optic zone of the ophthalmic device. The front, intermediate and back insert piece may have either or both of their surfaces curved in various manners, and in some examples the radius of curvature of a back surface on the front insert piece may be approximately the same as the radius of curvature of the front surface of the intermediate insert piece. An energy source may be included into the lens and into the insert, and in some examples the energy source may be located wherein at least a portion of the energy source is in the non-optic zone of the device.

The insert with a front insert piece, a back insert piece and at least a first intermediate insert piece may comprise at least a first liquid crystal molecule, and the liquid crystal molecule or molecules may also be found in polymer networked regions of interstitially located liquid crystal molecules. In some examples, there may be a smoothly varying pattern formed by various manners into alignment layers which may then cause the liquid crystal molecules or networks of liquid crystal material to form cycloidal patterns. In some examples of cycloidal patterns, the locations in liquid crystal orientation aligning with a radial axis across at least a first portion of the optic insert may have a parabolic dependence on a radial dimension. The cycloidal pattern may have a primarily parabolic dependence on the radial distance, and in some examples, the cycloidal pattern may have parabolic and higher order parametric dependence on the radial distance from a center of the optic device.

In some examples with a front insert piece, a back insert piece and at least a first intermediate insert piece the ophthalmic device may be a contact lens.

In some examples the insert of the ophthalmic device with a front insert piece, a back insert piece and at least a first intermediate insert piece may comprise electrodes made of various materials, including transparent materials such as ITO as a non-limiting example. A first electrode may be located proximate to a back surface of a front curve piece, and a second electrode may be located proximate to a front surface of an intermediate piece. When an electric potential is applied across the first and second electrodes, an electric field may be established across a liquid crystal layer located between the electrodes. The application of an electric field across the liquid crystal layer may cause liquid crystal molecules within the layer to physically align with the electric field. In some examples, the liquid crystal molecules may be located in polymer networked regions of interstitially located liquid crystal material. When the liquid crystal molecules align with the electric filed, the alignment may cause a change in the optical characteristics that a light ray may perceive as it traverses the layer containing liquid crystal molecules. A non-limiting example may be that the index of refraction may be altered by the change in alignment. In some examples, the change in optical characteristics may result in a change in focal characteristics of the lens which contains the layer containing liquid crystal molecules.

In some examples the intermediate piece may comprise multiple pieces that are joined together.

In some examples where the insert device may be comprised of a front insert piece, a back insert piece and an intermediate piece or pieces, a liquid crystal containing layer may be located between the front insert piece and the intermediate piece or between the intermediate piece and the back insert piece. In addition, a polarizing element may be located within the variable insert device as well. The variable insert may comprise at least a portion which may be located in the optic zone of the ophthalmic device. The front, intermediate and back insert pieces may have either or both of their surfaces curved in various manners, and in some examples the radius of curvature of a back surface on the front insert piece may be approximately the same as the radius of curvature of the front surface of the intermediate insert piece. An energy source may be included into the lens and into the insert and in some examples the energy source may be located wherein at least a portion of the energy source is in the non-optic zone of the device.

In some examples it may be possible to reference surfaces within the variable optic insert rather than pieces. In some examples, an ophthalmic lens device may be formed where a variable optic insert may be positioned within the ophthalmic lens device where at least a portion of the variable optic insert may be positioned in the optical zone of the lens device. These examples may include a curved front surface and a curved back surface. In some examples the front surface and the back surface may be configured to form at least one chamber. The ophthalmic lens device may also include an energy source embedded in the insert in at least a region comprising a non-optical zone. The ophthalmic lens device may also include a layer containing liquid crystal material positioned within the chamber, wherein the layer includes regions of liquid crystal material aligned in a cycloidal pattern in the plane of the local surface of the lens. The ophthalmic lens device may also include a layer where the locations in liquid crystal orientation aligning with a radial axis across at least a first portion of the optic insert may have a parabolic dependence on a radial dimension.

In some examples a contact lens device may be formed where a variable optic insert may be positioned within the ophthalmic lens device where at least a portion of the variable optic insert may be positioned in the optical zone of the lens device. These examples may include a curved front surface and a curved back surface. In some examples the front surface and the back surface may be configured to form at least a first chamber. The contact lens device may also include a layer containing liquid crystal material positioned within the chamber, wherein the layer includes regions of liquid crystal material aligned in a cycloidal pattern.

In some examples a contact lens device may be formed where a variable optic insert may be positioned within the ophthalmic lens device where at least a portion of the variable optic insert may be positioned in the optical zone of the lens device. The contact lens device may also include a layer containing liquid crystal material positioned within the chamber, wherein the layer includes regions of liquid crystal material aligned in a cycloidal pattern, and wherein at least a first surface of the layer may be curved.

In some examples an ophthalmic lens device may be formed where a variable optic insert may be positioned within the ophthalmic lens device where at least a portion of the variable optic insert may be positioned in the optical zone of the lens device. These examples may include a curved front surface and a curved back surface. In some examples a first curved front surface and a first curved back surface may be configured to form at least a first chamber. A second curved front surface and a second curved back surface may be configured to form at least a second chamber. The ophthalmic lens device may also include a layer containing liquid crystal material positioned within the first chamber, wherein the layer includes regions of liquid crystal material aligned in a cycloidal pattern. The ophthalmic lens device may also include an energy source embedded in the insert in at least a region comprising a non-optical zone. In some examples the ophthalmic lens may be a contact lens. In some examples the ophthalmic lens may be an intraocular lens.

In some examples a contact lens device may be formed where a variable optic insert may be positioned within the ophthalmic lens device where at least a portion of the variable optic insert may be positioned in the optical zone of the lens device. The contact lens may include a curved first front surface and a curved first back surface wherein the first front surface and the first back surface are configured to form at least a first chamber. The contact lens may also include a first layer of electrode material proximate to the back surface of the curved first front surface. The contact lens may also comprise a second layer of electrode material proximate to the front surface of the first back curve piece. The contact lens may also include a first layer containing liquid crystal material positioned within the first chamber, wherein the layer includes regions of liquid crystal material aligned in a pattern wherein an index of refraction across at least a first portion of the variable optic insert varies with a radial, wherein the first layer containing liquid crystal material varies its index of refraction affecting a ray of light traversing the first layer of liquid crystal material when an electric potential is applied across the first layer of electrode material and the second layer of electrode material. The contact lens device may additionally include a curved second front surface and a curved second back surface wherein the second front surface and the second back surface are configured to form at least a second chamber. The contact lens device may also comprise a third layer of electrode material proximate to the back surface of the curved second front surface, and a fourth layer of electrode material proximate to the front surface of the second back curve piece. A second layer containing liquid crystal material positioned within the second chamber may also be included wherein the layer includes regions of liquid crystal material aligned in a cycloidal pattern, and wherein the second layer containing liquid crystal material varies its index of refraction affecting a ray of light traversing the first layer containing liquid crystal material when an electric potential is applied across the third layer of electrode material and the forth layer of electrode material. The introduction of an electrical potential across layers of electrode material may erase a cycloidal pattern in a liquid crystal layer in proximity to the electrodes. The contact lens may also include an energy source embedded in the insert in at least a region comprising a non-optical zone. The contact lens may also include an electrical circuit comprising a processor, wherein the electrical circuit controls the flow of electrical energy from the energy source to one or more of the first, second, third or fourth electrode layers. And, the contact lens' variable optic insert may also alter a focal characteristic of the ophthalmic lens.

BRIEF DESCRIPTION OF THE DRAWINGS

The foregoing and other features and advantages of the invention will be apparent from the following, more particular description of preferred examples of the invention, as illustrated in the accompanying drawings.

DETAILED DESCRIPTION OF THE INVENTION

Figure 1:
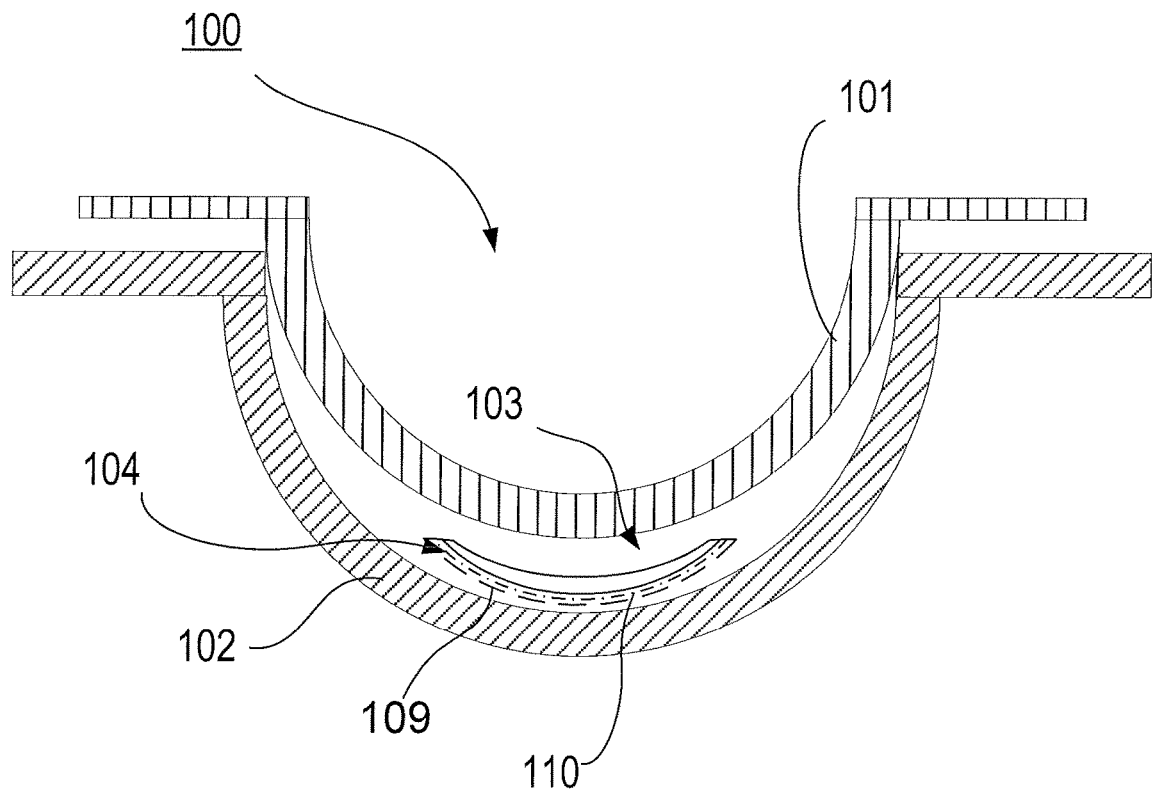
FIG. 1 illustrates exemplary mold assembly apparatus components that may be useful in implementing some examples of the present invention.

The present invention includes methods and apparatus for manufacturing an ophthalmic lens with a variable optic insert wherein the variable optic portion is comprised of a liquid crystal or a composite material which itself includes liquid crystal constituents. In addition, the present invention includes an ophthalmic lens with a variable optic insert comprised of liquid crystal incorporated into the ophthalmic lens.

According to the present invention, an ophthalmic lens is formed with an embedded insert and an energy source, such as an electrochemical cell or battery as the storage means for the Energy. In some examples, the materials comprising the energy source may be encapsulated and isolated from an environment into which an ophthalmic lens is placed. In some examples the energy source may include an electrochemical cell chemistry which may be used in a primary or rechargeable configuration.

A wearer-controlled adjustment device may be used to vary the optic portion. The adjustment device may include, for example, an electronic device or passive device for increasing or decreasing a voltage output or engaging and disengaging the energy source. Some examples may also include an automated adjustment device to change the variable optic portion via an automated apparatus according to a measured parameter or a wearer input. Wearer input may include, for example, a switch controlled by wireless apparatus. Wireless may include, for example, radio frequency control, magnetic switching, patterned emanations of light, and inductance switching. In other examples activation may occur in response to a biological function or in response to a measurement of a sensing element within the ophthalmic lens. Other examples may result from the activation being triggered by a change in ambient lighting conditions as a non-limiting example.

Variation in optic power may occur when electric fields, created by the energization of electrodes, causes realignment within the liquid crystal layer thereby shifting the molecules from the resting orientation to an energized orientation. In other alternative examples, different effects caused by the alteration of liquid crystal layers by energization of electrodes may be exploited such as, for example, changing of the light polarization state, particularly, polarization rotation.

In some examples with liquid crystal layers, there may be elements in the non-optical zone portion of the ophthalmic lens that may be energized, whereas other examples may not require energization. In the examples without energization, the liquid crystal may be passively variable based on some exterior factor, for example, ambient temperature, or ambient light.

An alternative example may derive when the physical lens elements that contain the liquid crystal layers are shaped themselves to have different focal characteristics. The electrically variable index of refraction of a liquid crystal layer may then be used to introduce changes in the focal characteristics of the lens based on the application of an electric field across the liquid crystal layer through the use of electrodes. The index of refraction of a liquid crystal layer may be referred to as an effective index of refraction, and it may be possible to consider each treatment relating to an index of refraction as equivalently referring to an effective index of refraction. The effective index of refraction may come, for example, from the superposition of multiple regions with different indices of refraction. In some examples, the effective aspect may be an average of the various regional contributions, while in other examples the effective aspect may be a superposition of the regional or molecular effects upon incident light. The shape that the front containment surface makes with the liquid crystal layer and the shape that the back containment surface makes with the liquid crystal layer may determine, to first order, the focal characteristics of the system. While referring to refractive characteristics of the liquid crystal layer, the patterning of these refractive characteristics may impart to the lens diffractive characteristics that are used to effectively alter focal characteristics of the lens.

In the following sections detailed descriptions of examples of the invention will be given. The description of both preferred and alternative examples are examples only, and it is understood that to those skilled in the art that variations, modifications and alterations may be apparent. It is therefore to be understood that said examples do not limit the scope of the underlying invention.

GLOSSARY

In this description and claims directed to the presented invention, various terms may be used for which the following definitions will apply:

Alignment layer: as used herein refers to a layer adjacent to a liquid crystal layer that influences and aligns the orientation of molecules within the liquid crystal layer. The resulting alignment and orientation of the molecules may affect light that passes through the liquid crystal layer. For example, the alignment and orientation may act with refractive characteristics upon the incident light. Additionally, the effect may include alteration of the polarization of the light.

Cycloidal: used herein, cycloidal refers to an optical axis orientation pattern resembling the orientation pattern of a line segment connecting opposite points in a circle as the circle moves on a surface. As used herein, cycloidal also refers to curves resulting from mathematical transformations, such as linear and non-linear contraction or expansion transformations, rotational transformations and the like, performed upon the pattern of a line segment connecting opposite points in a circle as the circle moves on a surface.

Electrical Communication: as used herein refers to being influenced by an electrical field. In the case of conductive materials, the influence may result from or in the flow of electrical current. In other materials, it may be an electrical potential field that causes an influence, such as the tendency to orient permanent and induced molecular dipoles along field lines as an example.

Energized: as used herein refers to the state of being able to supply electrical current to or to have electrical energy stored within.

Energized orientation: as used herein refers to the orientation of the molecules of a liquid crystal when influenced by an effect of a potential field powered by an energy source. For example, a device containing liquid crystals may have one energized orientation if the energy source operates as either on or off. In other examples, the energized orientation may change along a scale affected by the amount of energy applied.

Energy: as used herein refers to the capacity of a physical system to do work. Many uses within this invention may relate to the said capacity being able to perform electrical actions in doing work.

Energy source: as used herein refers to device capable of supplying energy or placing a biomedical device in an energized state.

Energy Harvesters: as used herein refers to device capable of extracting energy from the environment and convert it to electrical energy.

Interstices and Interstitial as used herein refer to regions within the boundaries of a polymer networked layer that are unoccupied by portions of the polymer and may be locations for other atoms or molecules to reside. Typically, herein, a liquid crystal molecule itself may co-reside in a region within the polymer network and the space that said liquid crystal therefore occupies may be classified as an interstice.

Intraocular lens: as used herein refers to an ophthalmic lens that is embedded within the eye.

Lens-Forming Mixture or Reactive Mixture or reactive monomer mixture (RMM): as used herein refers to a monomer or prepolymer material that may be cured and crosslinked or crosslinked to form an ophthalmic lens. Various examples may include lens-forming mixtures with one or more additives such as: UV blockers, tints, photoinitiators or catalysts, and other additives one might desire in an ophthalmic lens such as, for example, contact or intraocular lenses.

Lens-Forming Surface: as used herein refers to a surface that is used to mold a lens. In some examples, any such surface may have an optical quality surface finish, which indicates that it is sufficiently smooth and formed so that a lens surface fashioned by the polymerization of a lens-forming mixture in contact with the molding surface is optically acceptable. Further, in some examples, the lens-forming surface may have a geometry that is necessary to impart to the lens surface the desired optical characteristics, including, for example, spherical, aspherical and cylinder power, wave front aberration correction, and corneal topography correction.

Liquid Crystal: as used herein refers to a state of matter having properties between a conventional liquid and a solid crystal. A liquid crystal may not be characterized as a solid, but its molecules exhibit some degree of alignment. As used herein, a liquid crystal is not limited to a particular phase or structure, but a liquid crystal may have a specific resting orientation. The orientation and phases of a liquid crystal may be manipulated by external forces, for example, temperature, magnetism, or electricity, depending on the class of liquid crystal.

Lithium Ion Cell: as used herein refers to an electrochemical cell where Lithium ions move through the cell to generate electrical energy. This electrochemical cell, typically called a battery, may be reenergized or recharged in its typical forms.

Media insert or insert: as used herein refers to a formable or rigid substrate capable of supporting an energy source within an ophthalmic lens. In some examples, the media insert also includes one or more variable optic portions.

Mold: as used herein refers to a rigid or semi-rigid object that may be used to form lenses from uncured formulations. Some preferred molds include two mold parts forming a front curve mold part and a back curve mold part.

Ophthalmic Lens or Lens: as used herein refers to any ophthalmic device that resides in or on the eye. These devices may provide optical correction or modification, or may be cosmetic. For example, the term "lens" may refer to a contact lens, intraocular lens, overlay lens, ocular insert, optical insert, or other similar device through which vision is corrected or modified, or through which eye physiology is cosmetically enhanced (e.g. iris color) without impeding vision. In some examples, the preferred lenses of the invention are soft contact lenses which are made from silicone elastomers or hydrogels, which include, for example, silicone hydrogels and fluorohydrogels.

Optical or optic zone: as used herein refers to an area of an ophthalmic lens through which a wearer of the ophthalmic lens sees.

Power: as used herein refers to work done or energy transferred per unit of time.

Rechargeable or Reenergizable: as used herein refers to a capability of being restored to a state with higher capacity to do work. Many uses within the present invention may relate to the capability of being restored with the ability to flow electrical current at a certain rate for certain, reestablished time period.

Reenergize or Recharge: as used herein refers to the restoration of an energy source to a state with higher capacity to do work. Many uses within the present invention may relate to restoring a device to the capability to flow electrical current at a certain rate for a certain, reestablished time period.

Released from a mold: as used herein refers to a lens is either completely separated from the mold, or is only loosely attached so that it may be removed with mild agitation or pushed off with a swab.

Resting orientation: as used herein refers to the orientation of the molecules of a liquid crystal device in its resting, non-energized state.

Variable optic: as used herein refers to the capacity to change an optical quality, for example, the optical power of a lens or the polarizing angle.

Ophthalmic Lenses

Referring to FIG. 1, an to form ophthalmic devices comprising sealed and encapsulated inserts is depicted. The apparatus includes an exemplary front curve mold 102 and a matching back curve mold 101. A variable optic insert 104 and a body 103 of the ophthalmic device may be located inside the front curve mold 102 and the back curve mold 101. In some examples, the material of the body 103 may be a hydrogel material, and the variable optic insert 104 may be surrounded on all surfaces by this material.

The variable optic insert 104 may comprise multiple liquid crystal layers (also called layers containing liquid crystal.) Other examples may include a single liquid crystal layer, some of which are discussed in later sections. The use of the apparatus 100 may create a novel ophthalmic device comprised of a combination of components with numerous sealed regions.

In some examples, a lens with a variable optic insert 104 may include a rigid center soft skirt design wherein a central rigid optical element including the layer containing liquid crystal 109 and the layer containing liquid crystal 110 is in direct contact with the atmosphere and the corneal surface on respective anterior and posterior surfaces. The soft skirt of lens material (typically a hydrogel material) is attached to a periphery of the rigid optical element, and the rigid optical element may also add energy and functionality to the resulting ophthalmic lens.

Figure 2A:
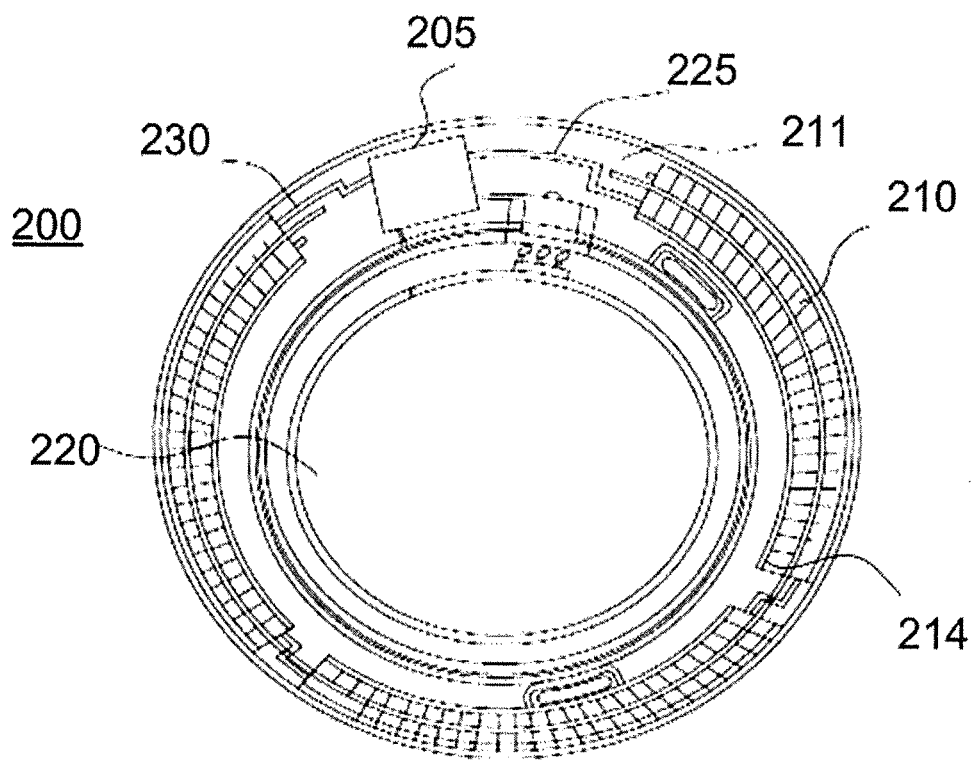
FIGS. 2A and 2B illustrate an exemplary energized ophthalmic lens with a variable optic insert embodiment.
Figure 2B:
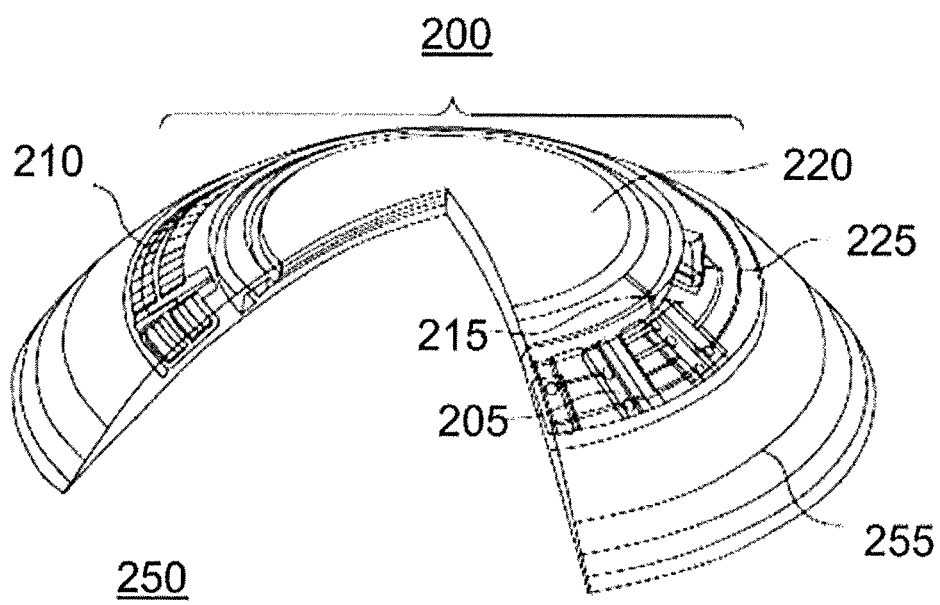

Referring to FIG. 2A, at 200 a top down and FIG. 2B at 250 a cross sectional depiction of an example of a variable optic insert is shown. In this depiction, an energy source 210 is shown in a periphery portion 211 of the variable optic insert 200. The energy source 210 may include, for example, a thin film, rechargeable lithium ion battery or an alkaline cell based battery. The energy source 210 may be connected to interconnect features 214 to allow for interconnection. Additional interconnects at 225 and 230 for example may connect the energy source 210 to a circuit such as electronic circuit 205. In other examples, an insert may have interconnect features deposited on its surface.

In some examples, the variable optic insert 200 may include a flexible substrate. This flexible substrate may be formed into a shape approximating a typical lens form in a similar manner previously discussed or by other means. However to add additional flexibility, the variable optic insert 200 may include additional shape features such as radial cuts along its length. There may be multiple electronic components such as that indicated by 205 such as integrated circuits, discrete components, passive components and such devices that may also be included.

A variable optic portion 220 is also illustrated. The variable optic portion 220 may be varied on command through the application of a current through the variable optic insert which in turn may typically vary an electric field established across a liquid crystal layer. In some examples, the variable optic portion 220 comprises a thin layer comprising liquid crystal between two layers of transparent substrate. There may be numerous manners of electrically activating and controlling the variable optic component, typically through action of the electronic circuit 205. The electronic circuit, 205 may receive signals in various manners and may also connect to sensing elements which may also be in the insert such as item 215. In some examples, the variable optic insert may be encapsulated into a lens skirt 255, which may be comprised of hydrogel material or other suitable material to form an ophthalmic lens. In these examples the ophthalmic lens may be comprised of the lens skirt 255 and an encapsulated variable optic insert 200 which may itself comprise layers or regions of liquid crystal material or comprising liquid crystal material and in some examples the layers may comprise polymer networked regions of interstitially located liquid crystal material.

A Variable Optic Insert Including Liquid Crystal Elements

Figure 3:
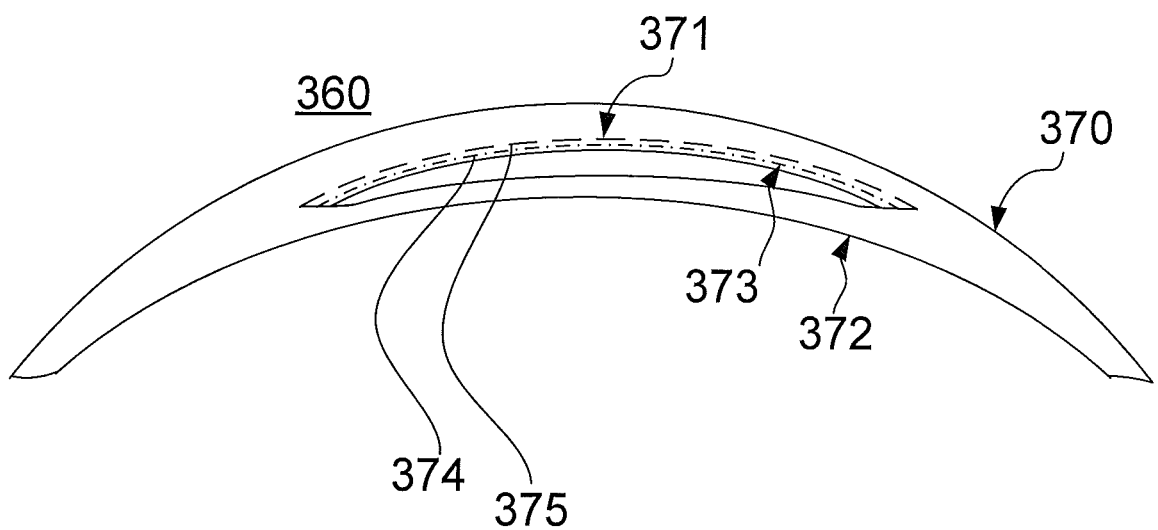
FIG. 3 illustrates a cross sectional view of an ophthalmic lens device embodiment with a variable optic insert wherein the variable optic portion may be comprised of cycloidally oriented liquid crystal.

Referring to FIG. 3, an ophthalmic lens 360 is shown with an embedded variable optic insert 371. The ophthalmic lens 360 may have a front curve surface 370 and a back curve surface 372. The variable optic insert 371 may have a variable optic portion 373 with a liquid crystal layer 374. In some examples, the variable optic insert 371 may have multiple liquid crystal layers 374 and 375. Portions of the variable optic insert 371 may overlap with the optical zone of the ophthalmic lens 360.

Figure 4A:
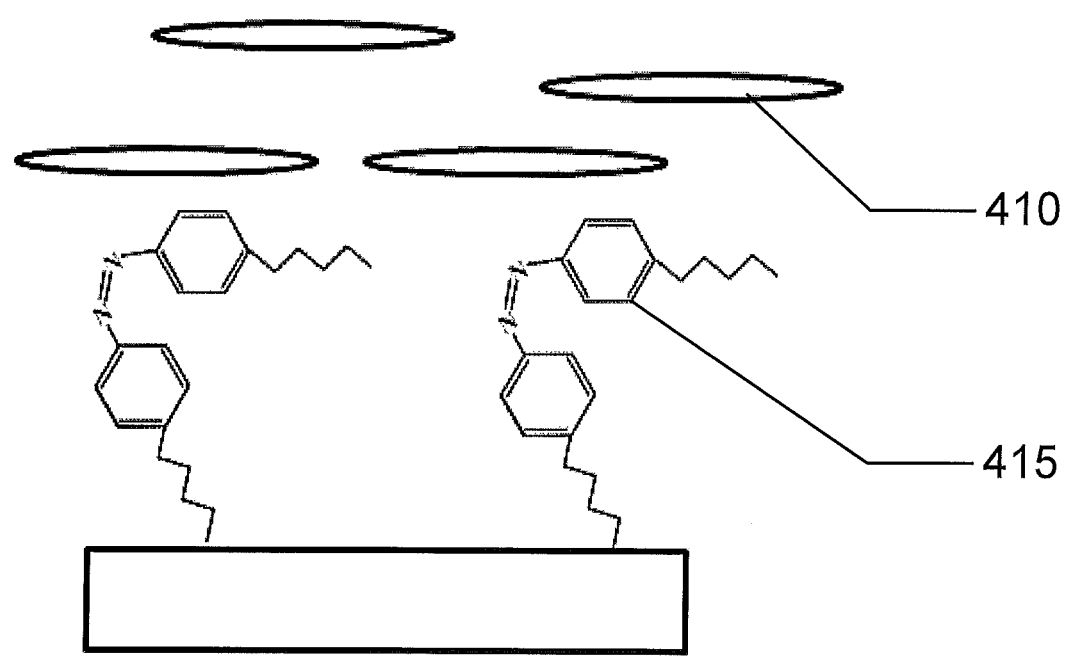
FIGS. 4A and 4B illustrate an exemplary interaction of alignment layers that may orient liquid crystal molecules in the plane of the surface but with different axial orientations.

Referring to FIG. 4A, a depiction of a alignment of liquid crystal molecules 410 by alignment layer molecules 415 may be depicted in an illustrative manner. As shown, alignment layers may be used to control the orientation of liquid crystal molecules relative to a surface that the alignment layer is attached to and also in the plane or local plane of that surface. The control of the orientation may itself control regional effective index of refraction of light progressing through the surface. As well, the orientation of the liquid crystal molecules in the local plane may cause interactions with the electric field vectors of light passing through the surface Thus, the control of the orientation of the liquid crystal molecules can form a regionally variable effective index of refraction or if many of the molecules are generally oriented in the same manner in the direction perpendicular to the surface then the orientation of the molecules within the plane of the local surface region may affect the phase of electromagnetic radiation or light that may pass through the region. Numerous manners of orienting the liquid crystal molecules in the plane may allow for different patterns in the liquid crystal spatial orientation in a programmable manner.

Referring again to FIG. 4A, a close up depiction of an example of alignment layer molecules 415 in an orienting layer interacting with liquid crystal molecules 410 may be found. In a non-limiting example, the alignment layer molecule may be an Azobenzene moiety. In some examples, one stabile configuration of the azobenzene moiety may place the aromatic ring portions of the moiety in a cis-configuration where the rings are located on the same side of an intervening double bonded chemical bond. This may be the configuration depicted at 415 and may result in a portion of the molecule being oriented parallel to the surface they are binding to. As depicted the interaction of the exemplary azobenzene moiety with liquid crystal molecules may cause them to align along the axes of the azobenzene moieties. In FIG. 4A these alignment molecules may be oriented to locate the liquid crystal molecules parallel to the surface. As shown, in addition within the plane of the surface the molecules are shown to orient liquid crystal molecules lengthwise across the page.

Figure 4B:
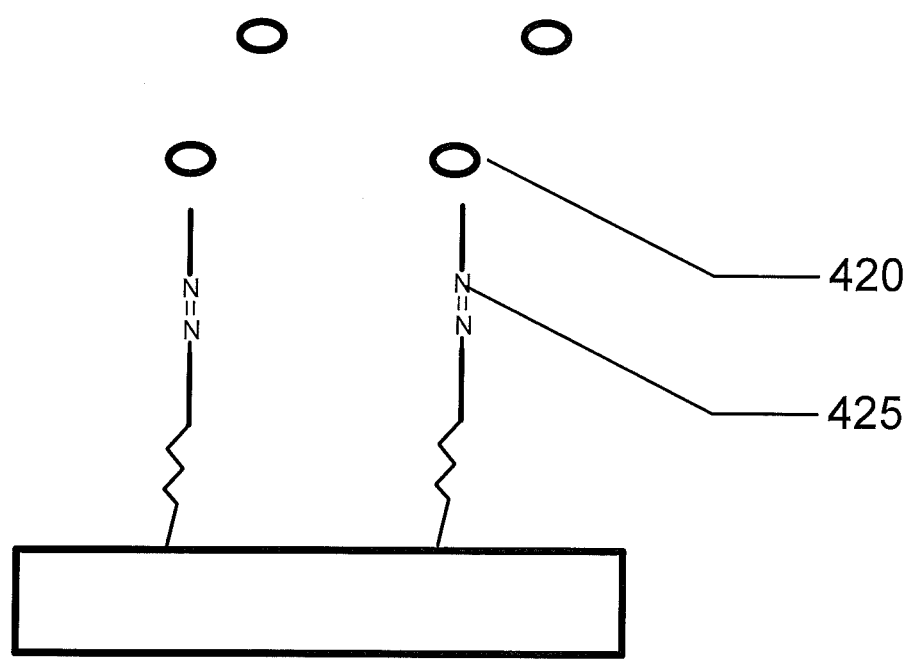

Referring to FIG. 4B, an alternative orientation may be found. In this example, the alignment layer molecules 425 may again be oriented in an exemplary cis configuration that aligns liquid crystal molecules 420 parallel to the local surface however now the orientation of these molecules then is illustrated to depict that another orientation within the plane may have the length of the liquid crystal molecules oriented in and out of the page. By programming the orientation of the alignment layer molecules it may be possible to define regions that are oriented at many orientations between that depicted in FIG. 4A and in FIG. 4B.

Ophthalmic Devices Comprising Cycloidal Waveplate Lens

A special variety of polarization holograms; namely, cycloidal diffractive waveplates (CDW), provide substantially one hundred percent diffraction efficiency and may be spectrally broadband. The structure of cycloidal diffractive waveplates, schematically illustrated in FIG. 5A, comprises anisotropic material film 565, wherein the optical axis orientation is continuously rotating in the plane of the film as illustrated by the pattern in the anisotropic material film 565. Nearly one hundred percent efficiency for visible wavelengths is achieved at fulfillment of a half-wave phase retardation condition typically met in approximately one micrometer (0.001 mm) thick liquid crystal polymer (LCP) films. Referring again to FIG. 5A, a close up view of the orientation programming that may occur in a cycloidal waveplate design shows the repetitively cycling pattern. In a given axis direction, 563 for example which may be referred to as the x axis, the pattern may vary from orientation parallel to the axial direction 560 through orientations towards a perpendicular orientation to the axial direction 561 and again back through a parallel orientation to the axial direction at 562.

Figure 5A:
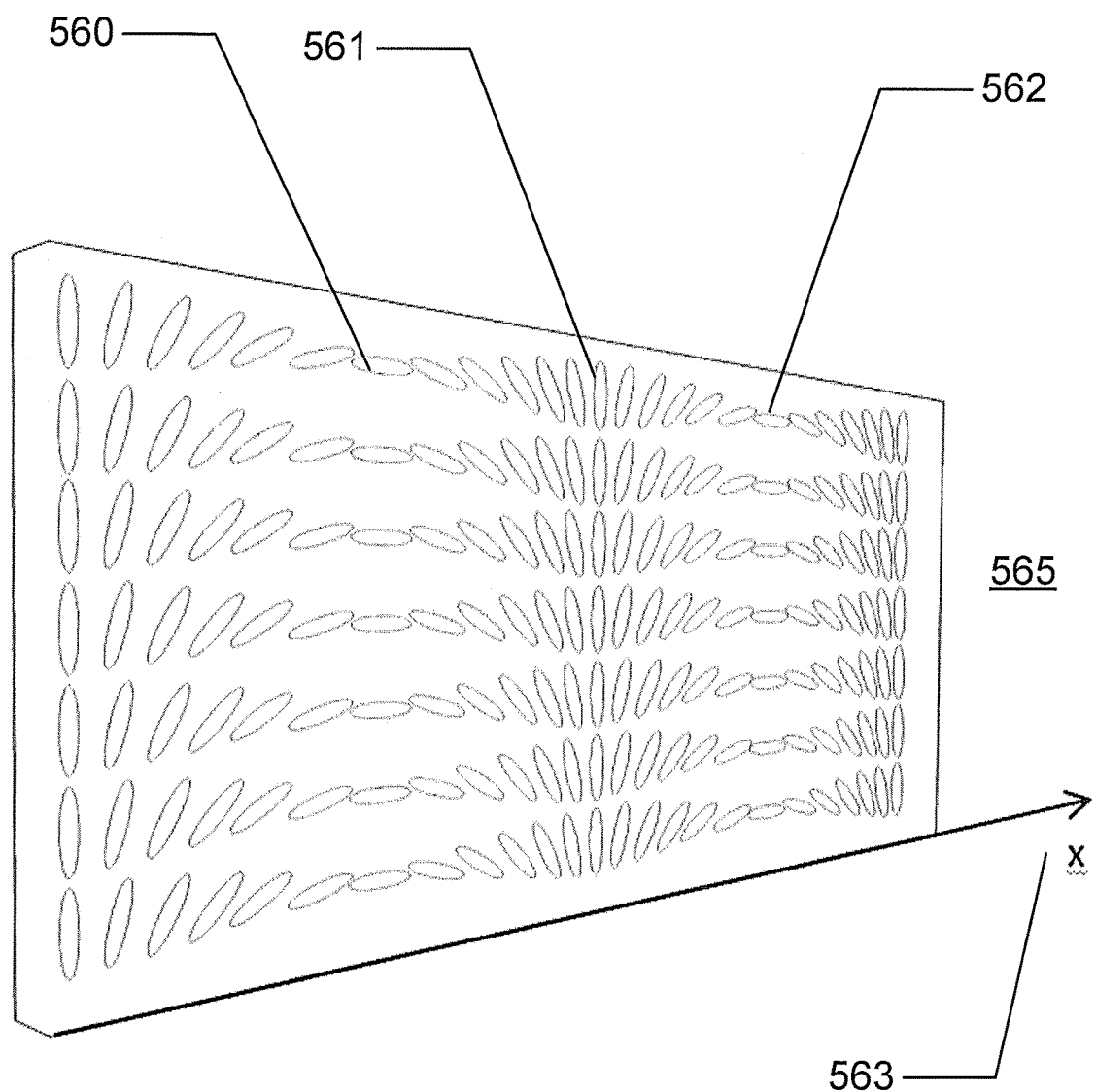
FIG. 5A illustrates an example of a diffractive waveplate according to the present disclosure.
Figure 5B:
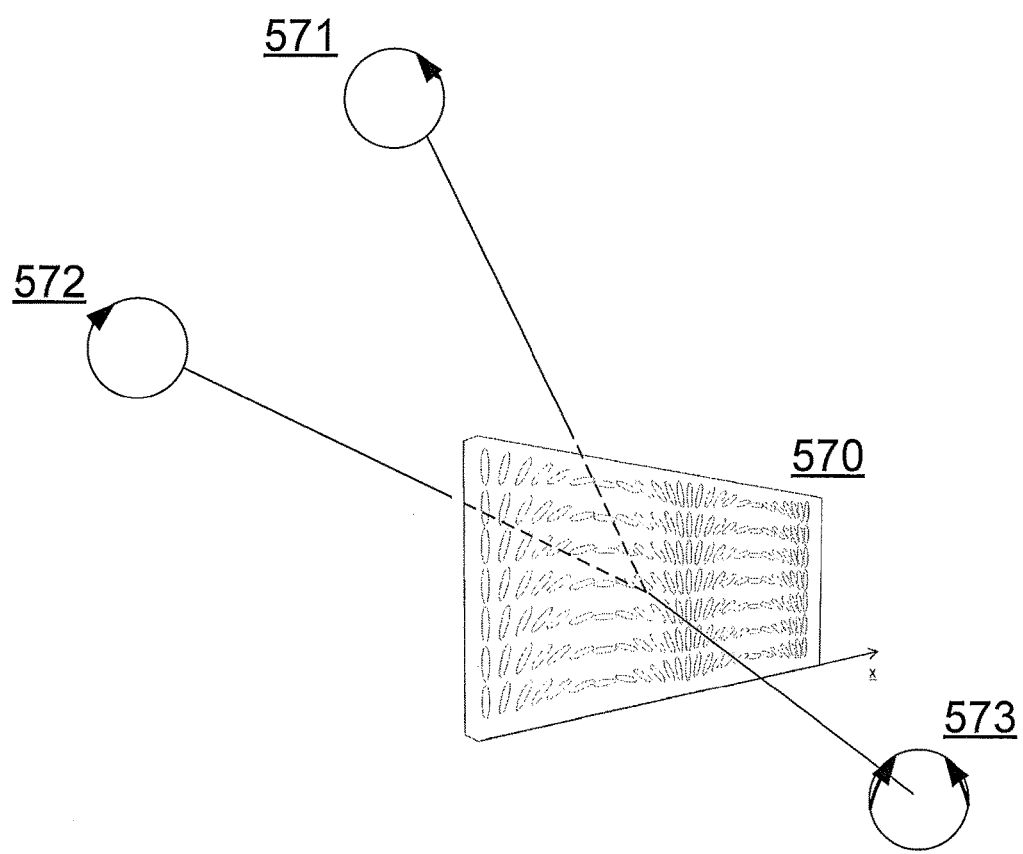
FIG. 5B illustrates an example of the interaction of circular polarization components of light with diffractive waveplates.

Such an unusual situation in optics where a thin grating exhibits high efficiency, may be understood by considering a linearly polarized light beam of wavelength $\lambda$ incident normally, along the z-axis, on a birefringent film in the x,y plane. If the thickness of the film L and its optical anisotropy, $\Delta n$, are chosen such that $L\Delta n=\lambda/2$, and its optical axis is oriented at forty-five (45) degrees, angle $\alpha$, with respect to the polarization direction of the input beam, the polarization of the output beam is rotated by ninety (90) degrees, angle $\beta$. This is how half-wave waveplates function. The polarization rotation angle at the output of such a waveplate, $\beta=2\alpha$, depends on the orientation of the optical axis $d=(dx, dy)=(\cos \alpha, \sin \alpha)$. Liquid crystal materials, both low molecular weight as well as polymeric, allow continuous rotation of d in the plane of the waveplate at high spatial frequencies, $\alpha=qx$, where the spatial modulation period $\Lambda=2\pi/q$ may be comparable to the wavelength of visible light. Polarization of light at the output of such a waveplate is consequently modulated in space, $\beta=2qx$, and the electric field in the rotating polarization pattern at the output of this waveplate is averaged out, $<E>=0$, and there is no light transmitted in the direction of the incident beam. The polarization pattern thus obtained corresponds to the overlap of two circularly polarized beams propagating at the angles $\pm\lambda/\Lambda$. Referring to FIG. 5B, an illustration of this effect may be found. At 573, an incident beam comprising polarization components from both circular polarization patterns may intercept the exemplary cycloidal waveplate 570. The incident pattern is imaged into the two propagating angles for example $+\lambda/\Lambda$ at 571 and $-\lambda/\Lambda$ at 572. Only one of the diffraction orders is present in the case of a circularly polarized input beam, the $+1^{st}$ at 571 or $-1^{st}$ at 572, depending on whether the beam is right or left handed.

Figure 5C:
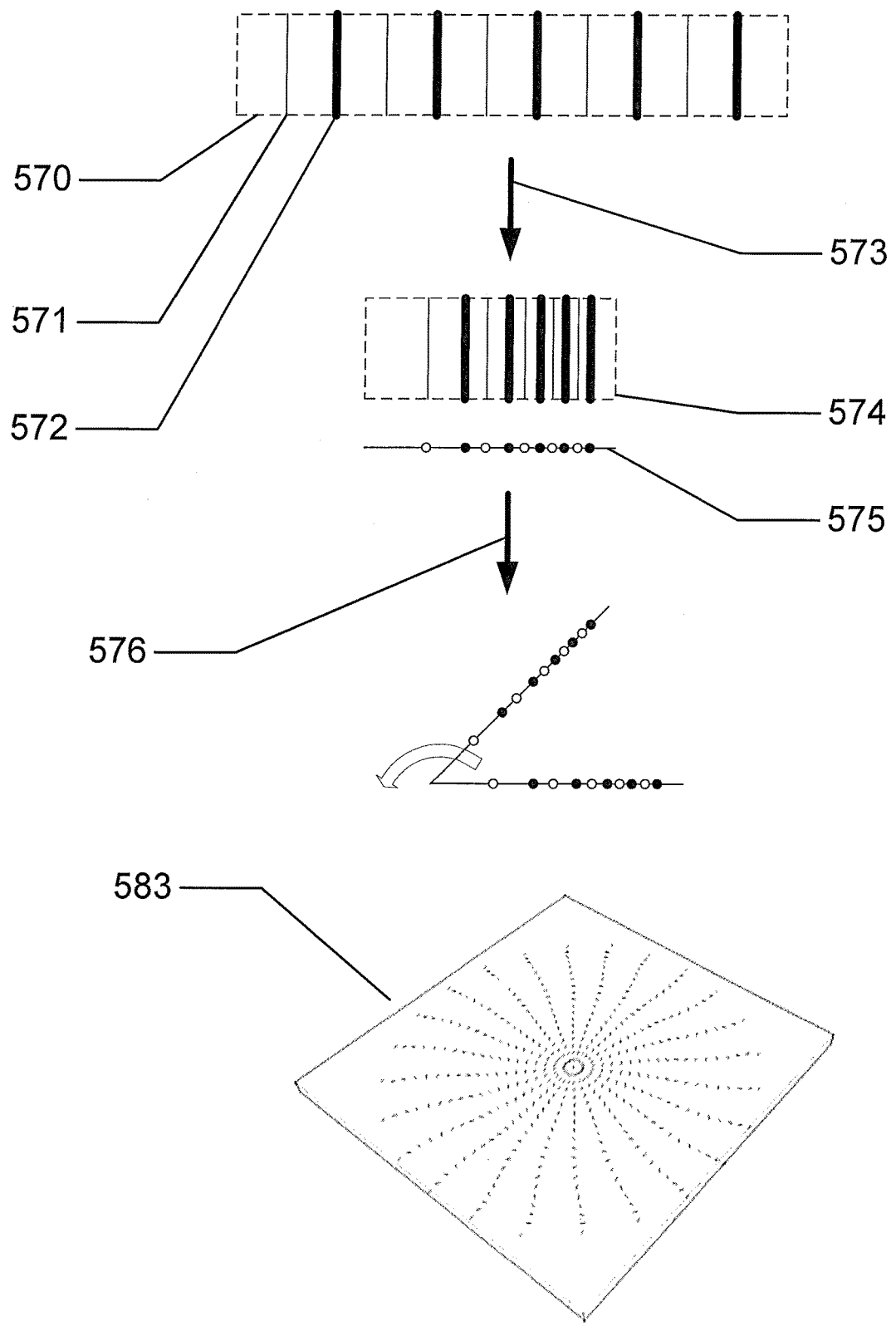
FIG. 5C illustrates a diffractive waveplate lens example and a model for transforming the diffractive waveplate example into a diffractive waveplate lens example.

A special variety of cycloidal diffractive waveplates may be illustrated at FIG. 5C. In such an example, the cycloidal diffractive waveplate pattern referred to in FIG. 5A may be further refined in the form factor of intraocular lens insert devices. In FIG. 5C a depiction of the conceptual permutation of the diffractive wave plate of FIG. 5A into a new pattern is depicted. A depiction of the orientation of liquid crystal molecules when looking down upon the diffractive waveplate is made in a simplified form 570. The simplified form 570 depicts molecules oriented parallel 571 to the axis direction 563 as a thin stripe, molecules oriented perpendicular 572 to the axis direction 563 are depicted with a thick line. In a cycloidal pattern, as shown in FIG. 5A, in between these two lines, the liquid crystal molecules may be modelled to smoothly vary in orientation between the extremes. The spacing of the lines in the simplified form 570 may be roughly linear. At 573, a transformation of the pattern may be made to make a parabolic contraction to the pattern.

Along the axis direction the spacing between the lines will therefore change, as depicted in the line location at simplified contracted form 574. An illustrative single line representation 575 of the simplified contracted form 574 now represents the narrow lines as unfilled circles and the thicker lines as filled circles. This representation may be useful to envision how the contracted cycloidal pattern may be formed into a closed patter. An exemplary manner of modelling the special variety of diffraction waveplate may be to consider rotating 576 the single line representation 575 of the contracted cycloidal pattern around an axis. In another example, the special variety of diffraction waveplate may be modelled by considering replicating the single line representation 575 around a circular path where each orientation at a particular radial point is the same around a completed circular path. In the resulting illustration 583, the shape is an estimation since it has been portrayed in a flattened manner, but a similar orientation programming shape may occur across three dimensional surfaces such as lens inserts as well.

Figure 5D:
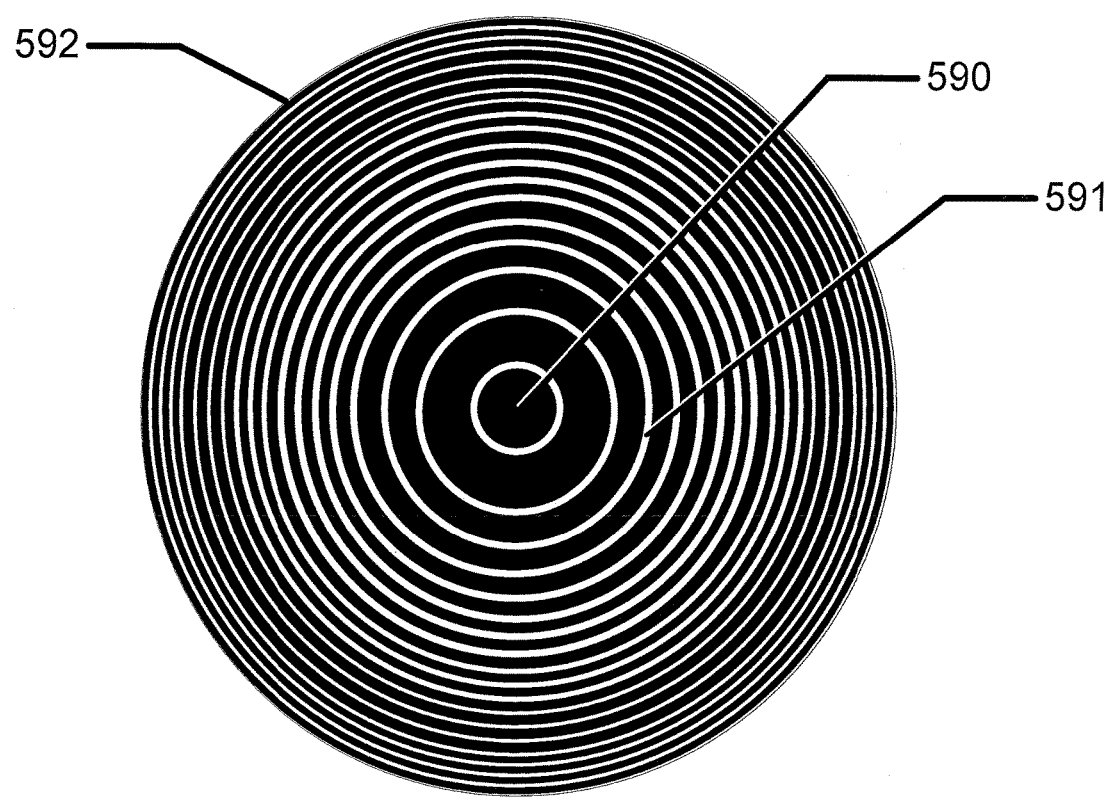
FIG. 5D illustrates a pattern that may occur when a lens of the type in FIG. 5C is placed between crossed polarizers.

The pattern that may result from these transformations may then be caused to occur in a liquid crystal layer by writing the appropriate alignment pattern into neighboring alignment layers. The writing of the alignment pattern may be performed upon a flat surface or upon a folded surface such as a subtended portion of a spherical surface. When the liquid crystal or liquid crystal polymer molecules are aligned in such a manner, and the resulting layer is placed between crossed polarizers, light emerging through the combination may form a pattern 592 such as that seen in FIG. 5D. The dark regions 590 may represent an orientation of the liquid crystal molecules in alignment with either of the crossed polarizer axes. The light areas 591 may represent regions where the molecules are aligned off the axes of the crossed polarization axes where the brightest points may be at roughly forty five degrees to either crossed polarizer axis. The parabolic aspect of the patterning may be estimated by the decreasing spacing between white pattern lines. Between consecutive white pattern lines, the cycloidal pattern may complete a cycle.

Figure 5E:
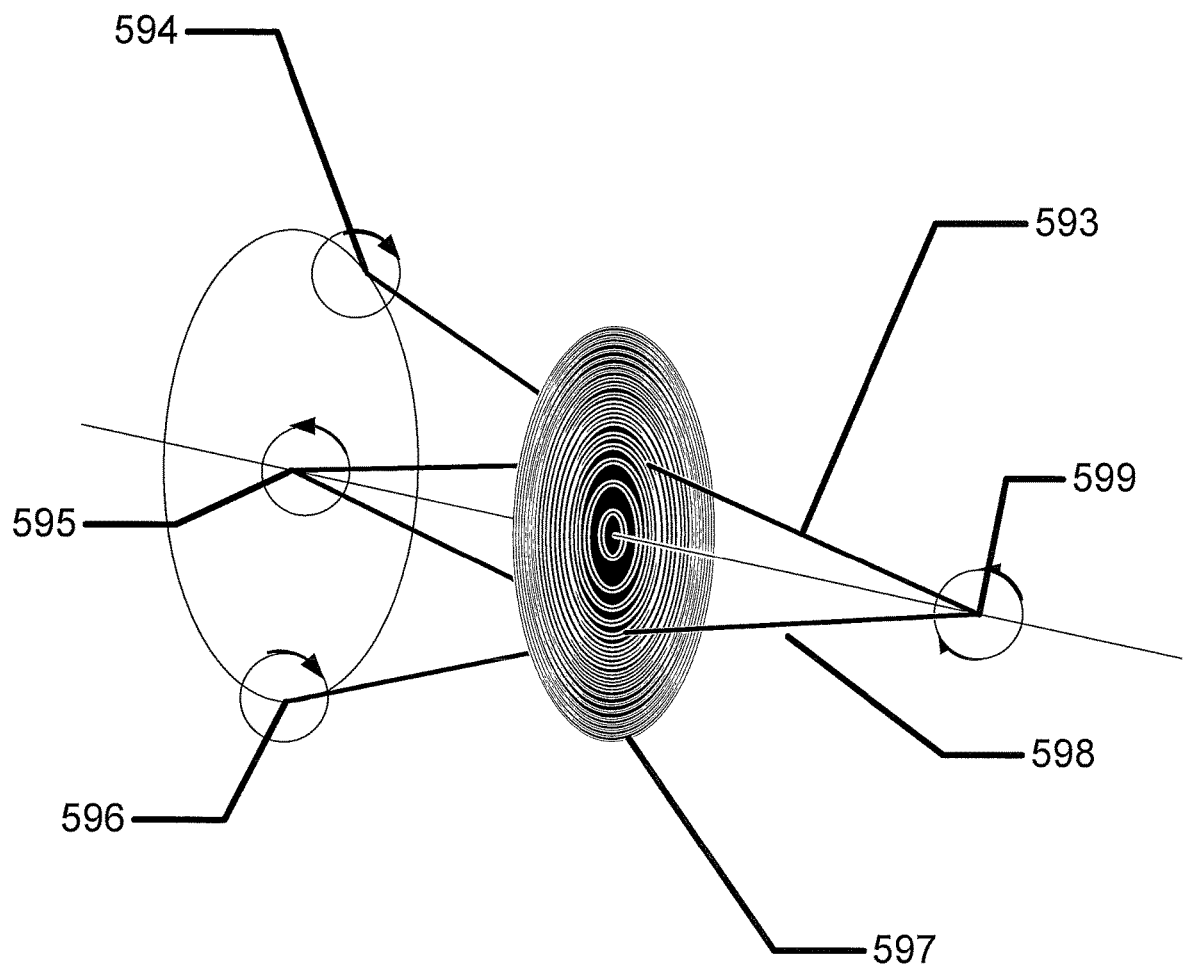
FIG. 5E illustrates how a cycloidal waveplate lens may function based on different polarizations of light.

Referring to FIG. 5E, an exemplary illustration of a diffractive waveplate lens of the type discussed herein, may be found. The focusing effect may derive from both the physical shape of the lens surface and the parabolic spacing superimposed over the cycloidal pattern, which may relate to a parabolic shape to the phase delay characteristics for light across the lens surface. The focusing characteristics may interact in a radial manner in the same model as has been discussed with the diffractive waveplate, where one circular polarization direction may be propagated at a $+1^{st}$ order and the other at a $-1^{st}$ order. In the exemplary illustration, an object 599 of some kind may be centrally located at a point and may be modelled by the exemplary rays 593 and 598. As these rays, shown with both circular polarization components interact with the diffractive waveplate lens 597 they may both be modelled to have a $+1^{st}$ order converged to an image at focal point 595 whereas the $-1^{st}$ order may be diverged from a focal point to diverged path 594 and diverged path 596 for the example of the exemplary rays. Thus a perceived image of an object for unpolarized light may be a superposition of a focused imaged and a defocussed image.

Such a diffractive waveplate lens structure acts like a lens with advantages compared to other Liquid Crystal lenses that may include that different or higher strength of the lens (measured as focal length or in diopters) may be obtained within the same thickness or thinner films. In some examples, the thickness of the film may be only 1-5 μm. Another advantage of the lens may be the opportunity of switching between positive and negative values for focal power adjustment by the switching of the polarization of light incident upon the device. In some examples, the use of a liquid crystal phase retardation plate may be used to facilitate the polarization switching. Decoupling between the lensing action and switching action may allow versatility in electrical characteristics of the system, such as capacitance and power consumption, as non-limiting examples. For example, even if the lens itself may be chosen to be thin, the thickness of the Liquid Crystal phase retarder may be chosen to minimize power consumption.

Figure 5F:
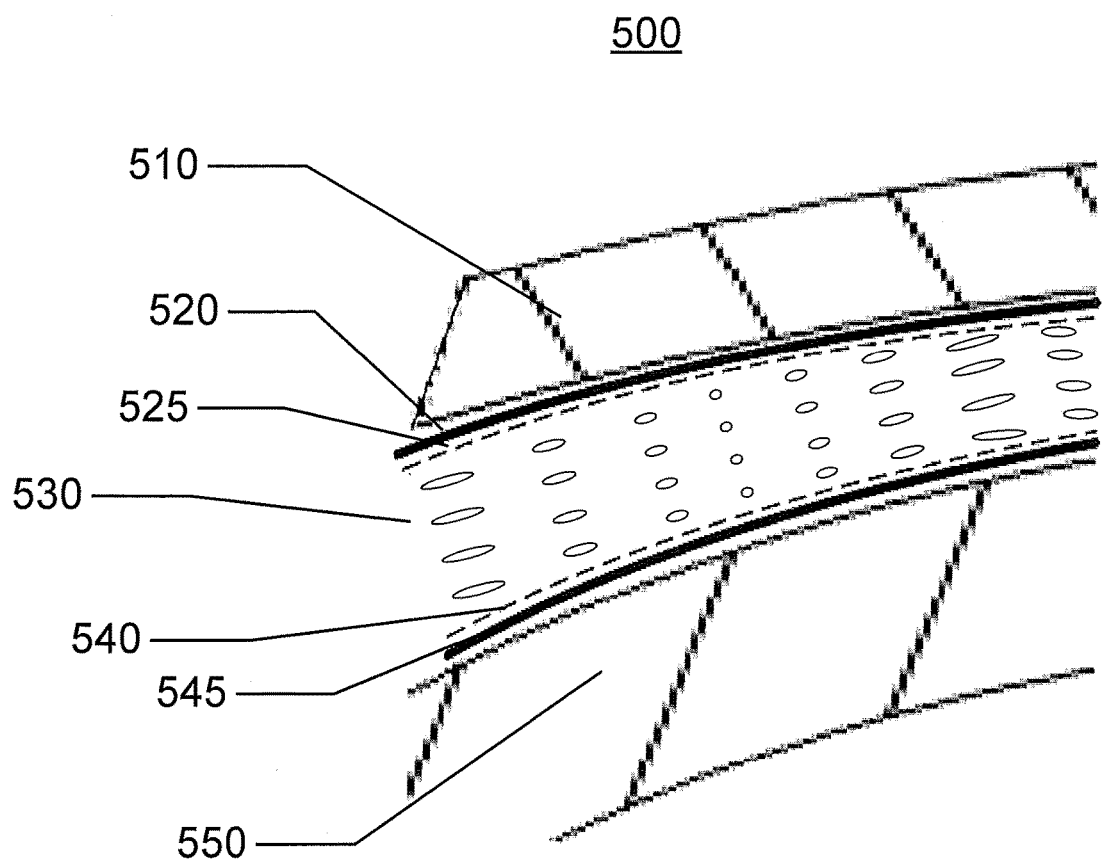
FIG. 5F illustrates a close-up of a cross section of an example of a variable optic insert wherein the variable optic portion may be comprised of cycloidally oriented liquid crystal layers in a non-energized state.

A cycloidal diffractive lens pattern formed within the space between a front insert piece and a back insert piece may form an electrically active embedded variable optic insert. Referring to FIG. 5F, a variable optic insert 500 that may be inserted into an ophthalmic lens is illustrated with an exemplary cycloidally varying index of refraction programmed through control of the orientation of the liquid crystal layer 530. The variable optic insert 500 may have a similar diversity of materials and structural relevance as has been discussed in other sections of this specification. In some examples, transparent electrodes at 520 and 545 may be placed on a first transparent substrate 510 and a second transparent substrate 550 respectively. The first 525 and second 540 lens surfaces may be comprised of a dielectric film, and the patterned alignment layers which may be placed upon the transparent electrodes or dielectric films respectively. The parabolic patterning superimposed upon the cycloidal orientation of the liquid crystal layers may introduce additional focusing power of the lens element above geometric effects.

Figure 5G:
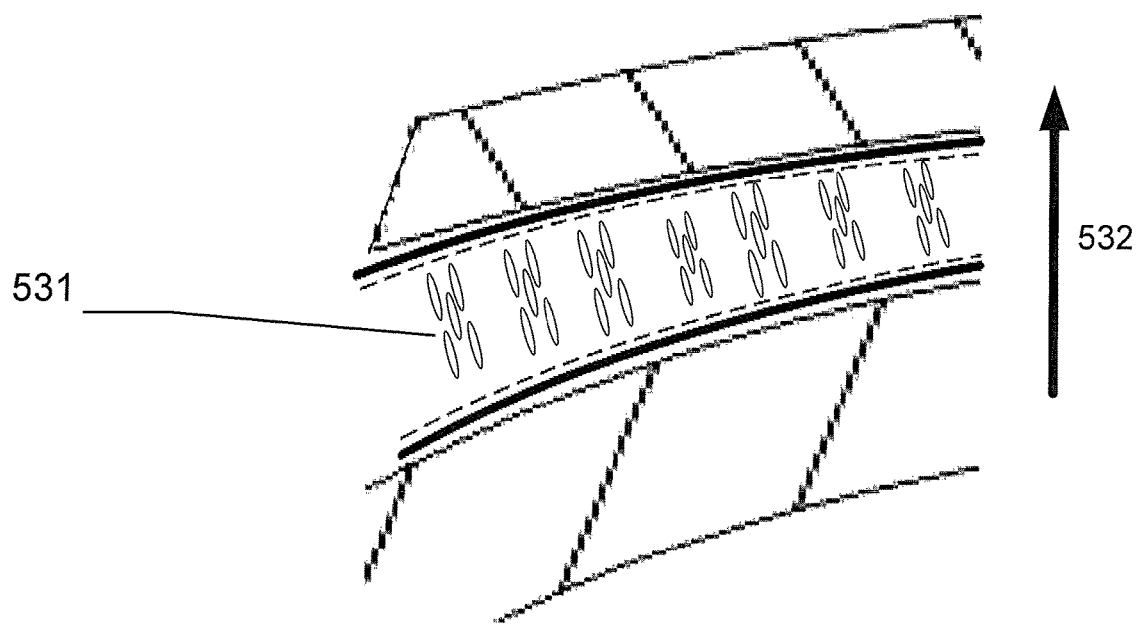
FIG. 5G illustrates a close-up of a cross section of an example of a variable optic insert wherein the variable optic portion may be comprised liquid crystal layers in an energized state.

As shown in FIG. 5G by the application of electric potential to electrodes in the front and back insert pieces an electric field 532 may be established across the cycloidally oriented liquid crystal layer. When liquid crystal moieties align with the electric field as depicted at 532, the resulting alignment may render the liquid crystal layer to become a spatially uniform film without the special properties of a diffractive waveplate lens. Thus, as a non-limiting example, a pattern at 531 that has an optical power may not cause a focusing effect with the application of an electric field as depicted at 532.

Examples of Diffractive Waveplate Lens Processing

Fabrication of Liquid Crystal and Liquid Crystal polymer diffractive waveplates may be a multistep process. The technology for printing cycloidal diffractive waveplates from a master waveplate may be fit for large-scale production with high quality and large areas. This may be compared to other examples involving holographic equipment which may add complexity, cost and stability problems. The printing technique may make use of the rotating polarization pattern obtained at the output of the master cycloidal diffractive waveplate from a linearly or circularly polarized input beam. The period of the printed waveplates may be doubled when one uses a linearly polarized input beam. As compared to direct recording in photoanisotropic materials, liquid crystal polymer technology based on photoalignment may have an advantage based upon the commercial availability of Liquid Crystal Polymers, for example, from Merck. A typical Liquid Crystal Polymer of reactive mesogens which may be referenced in a supplier's (Merck) nomenclature, such as RMS-001C, may be spin coated (typically three thousand (3000) rpm for sixty (60) s) on a photoalignment layer and UV polymerized for approximately ten (10) minutes. Multiple layers may be coated for broadband diffraction or for adjusting the peak diffraction wavelength.

In some examples an ophthalmic insert may be processed to incorporate a waveplate lens. In some examples a front optic piece may be molded, machined or otherwise formed in concert with a back optic piece to have a narrow gap to receive the liquid crystal material. In some examples, the gap may be as narrow as 1.5 microns. The nature of the desired gap thickness may be a function of the liquid crystal material and its coefficient of birefringence. A diffractive waveplate thickness may need to fulfill a first order or second order of the following equation—

$$\Delta n * d = (m_i + \tfrac{1}{2}) * \lambda$$

therefore a first order thickness ($m_i$=0) may be on the order of 1-2 um where a second order may be multiples of the first order thickness. d may represent the film thickness, delta n may represent the birefringence coefficient and lambda the wavelength at the center of the spectrum exposed to the device. The thickness may nevertheless be quite small, which may have desirable qualities for the size of the insert. In some examples, to maintain the thin gap at a uniform thickness, spacers of uniform size may be introduced into the liquid crystal material. Upon filling into the gap formed between the front optic and rear optic piece, the space may maintain a minimum gap thickness.

In some examples, the front optic and rear optic may be formed from Topas as an example. There may be surface treatments of the formed optic pieces that promote adhesion and film quality of electrode materials which may be deposited upon the optic pieces. The electrodes may be formed of the various discussed materials; and in an example may be comprised of ITO. In some examples, a dielectric film may be deposited upon the electrode material. An alignment layer may be placed upon the optic piece by spin coating. Examples of alignment layers may include various materials that may be summarized in the coming sections; for an example the material may include an example from a series of photo alignable azobenzene dyes (PAAD). Examples of the spin coating condition may be to rotate an approximately 1 cm diameter piece at a speed of 1000-5000 rotations per minute for 10-60 seconds or more.

Figure 6A:
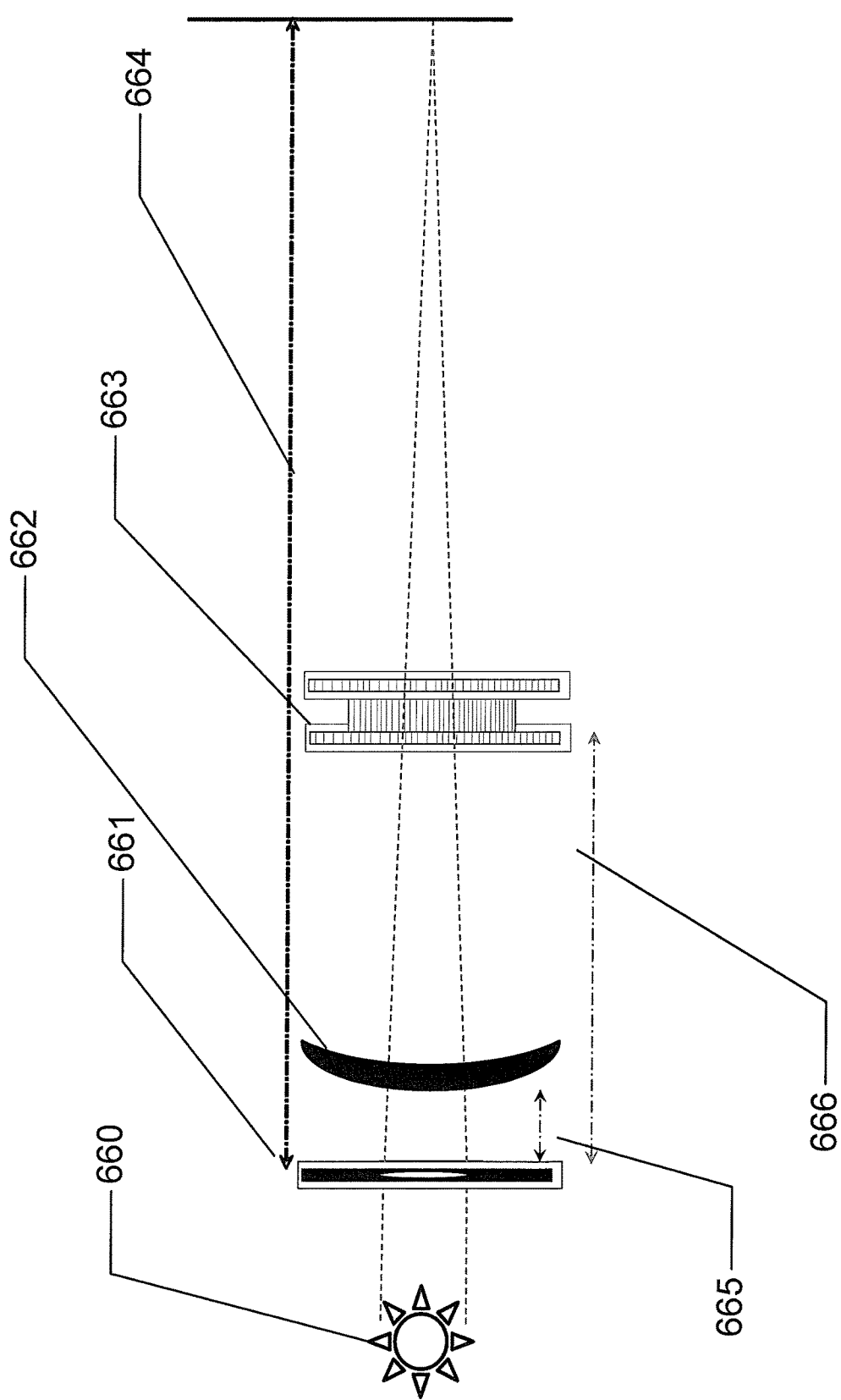
FIG. 6A illustrates aspects of methods and apparatus that may be used to form cycloidal waveplate lenses.

The optic pieces may be placed together without the presence of any liquid crystal material between the alignment layers. Next the photosensitive alignment layers may be patterned. Referring to FIG. 6A a depiction of an exemplary patterning process may be found. At 660 a coherent light sources such as a laser may irradiate a pattern mask. The coherent light source may have numerous wavelengths for operation, and for example may operate at 445 nm. The coherent light may pass through a holographic mask 661 that will pattern the cycloidal pattern as has been mentioned. The light may be concentrated through a focusing lens 662 that may be separated by an adjustable distance from the mask, for example 2 centimeters. The object of the focusing lens may be focused to a focal point 664 which may for example be about 40 cm. The focused pattern may intersect the front and back optic combined device 663 which may be located at the optic locating distance 666 which may be roughly 10 cm from the converging lens for example. The irradiation of the mask upon the photoalignment layer may proceed for a variable amount of time which may depend on the nature of the photoalignment layer. In an example the irradiation time may vary from 5 to 30 minutes at an intensity of incident light of 5-50 mW/cm$^2$. The resulting patterned lens pieces may then be filled with a liquid crystal containing material.

In some examples, as mentioned, the liquid crystal material may be a combination of different materials and may comprise liquid crystal, polymer liquid crystal and other such materials including the exemplary spacer spheres or other spacing devices. The result may be an insert that comprises a diffractive waveplate lens.

In some examples, an insert may be formed from a front optic piece with a back optic piece in similar manners to the previous example where a hybrid alignment condition is established. In such a condition, one of the front or back optic pieces may be patterned in a cycloidal type patterning whereas the other may be patterned such that the alignment layer is aligned all parallel to the surface of the optic piece or perpendicular to the surface of the optic piece. In some examples, the second optic piece may be coated with a different alignment material such as in a non-limiting sense octadecyldimethyl (3-trimethoxysilylpropyl) ammonium chloride which may be referred to as DMOAP. The DMAOP may be used to coat the optic piece and after drying may form a layer which aligns liquid crystal molecules in a homeotropic pattern, where the length of liquid crystal molecules is oriented perpendicularly to the surface.

Figure 6B:
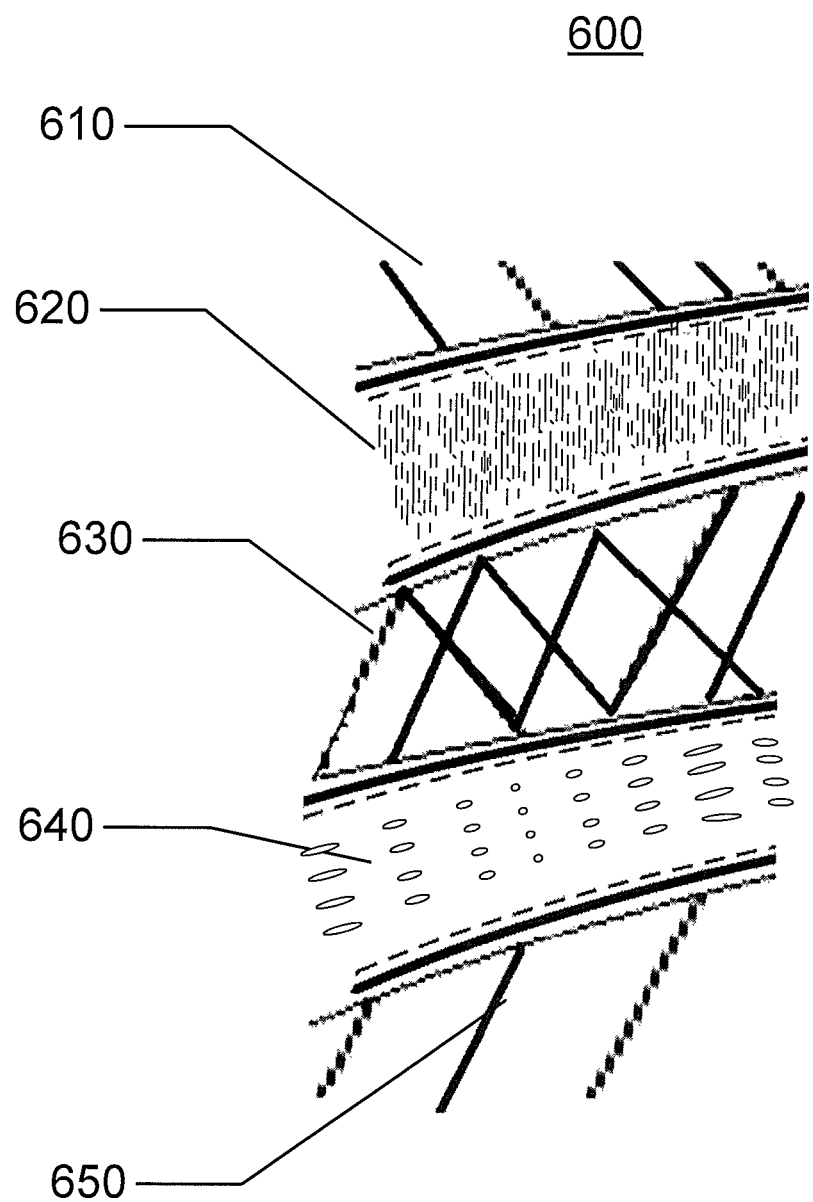
FIG. 6B illustrates an alternative embodiment of a variable optic lens comprising an insert wherein the variable optic portions may be comprised of cycloidal waveplate lens regions of liquid crystal molecules between shaped insert pieces and polarizing layers.

Referring to FIG. 6B, an alternative of a variable optic insert 600 that may be inserted into an ophthalmic lens is illustrated with second layer 620 and first layer 640. In some examples each of the layers may comprise liquid crystal layers; in other examples at least one of the layers comprises liquid crystal molecules in a waveplate lens type configuration. As discussed the waveplate lens may focus the two orientation vectors of circularly polarized light differentially. One may be focused while the other may be defocussed. In some examples, it may be desirable to create a two layer insert where a first layer may be a waveplate lens and the other may be a polarizing filter where that second layer filters out one circular polarization component of incident light. In other examples the second film may be configured to convert light to just one circular polarization component.

Each of the aspects of the various layers around the liquid crystal region(s) and if different the other layered region may have similar diversity as described in relation to the variable optic insert 500 in FIG. 5F. For exemplary purposes, the first layer 640 may be depicted to have waveplate lens type programming; whereas the second layer 620 may be depicted with a different orientation of liquid crystal molecules for this example. By combining a first liquid crystal based element formed by a first substrate 610, whose intervening layers in the space around 620 and a second substrate which may be called an intermediate substrate 630 may have a first filtering characteristic, with a second liquid crystal based element formed by a second surface on the intermediate substrate 630, the intervening layers in the space around 640 and a third substrate 650 with a waveplate focusing lens characteristic, a combination may be formed which may allow for an electrically variable focal characteristic of a lens with the clarity of only focused light permitted through the lens; as an example.

At the exemplary variable optic insert 600, a combination of at least the waveplate type lens layer of the various types and diversity associated with the examples at variable optic insert 500 may be formed utilizing three substrate layers. In other examples, the device may be formed by the combination of four different substrates. In such examples, the intermediate substrate 630 may be split into two layers. If the substrates are combined at a later time, a device that functions similarly to variable optic insert 600 may result. The combination of four layers may present an example for the manufacturing of the element where similar devices may be constructed around both 620 and 640 layers where the processing difference may relate to the portion of steps that define alignment features for a liquid crystal element.

Materials

Microinjection molding examples may include, for example, a poly (4-methylpent-1-ene) copolymer resin are used to form lenses with a diameter of between about 6 mm to 10 mm and a front surface radius of between about 6 mm and 10 mm and a rear surface radius of between about 6 mm and 10 mm and a center thickness of between about 0.050 mm and 1.0 mm. Some examples include an insert with diameter of about 8.9 mm and a front surface radius of about 7.9 mm and a rear surface radius of about 7.8 mm and a center thickness of about 0.200 mm and an edge thickness of about 0.050 mm.

The variable optic insert 104 illustrated in FIG. 1 may be placed in a mold part utilized to form an ophthalmic lens. The material of mold parts may include, for example, a polyolefin of one or more of: polypropylene, polystyrene, polyethylene, polymethyl methacrylate, and modified polyolefins. Other molds may include a ceramic or metallic material.

A preferred alicyclic co-polymer contains two different alicyclic polymers. Various grades of alicyclic co-polymers may have glass transition temperatures ranging from 105° C. to 160° C.

In some examples, the molds of the present invention may contain polymers such as polypropylene, polyethylene, polystyrene, polymethyl methacrylate, modified polyolefins containing an alicyclic moiety in the main chain and cyclic polyolefins. This blend may be used on either or both mold halves, where it is preferred that this blend is used on the back curve and the front curve consists of the alicyclic co-polymers.

In some preferred methods of making molds according to the present invention, injection molding is utilized according to known techniques, however, examples may also include molds fashioned by other techniques including, for example: lathing, diamond turning, forming, or laser cutting.

Typically, lenses are formed on at least one surface of both mold parts; back curve mold 101 and front curve mold 102. However, in some examples, one surface of a lens may be formed from a mold part and another surface of a lens may be formed using a lathing method, or other methods.

In some examples, a preferred lens material includes a silicone containing component. A "silicone-containing component" is one that contains at least one [—Si—O—] unit in a monomer, macromer or prepolymer. Preferably, the total Si and attached O are present in the silicone-containing component in an amount greater than about 20 weight percent, and more preferably greater than 30 weight percent of the total molecular weight of the silicone-containing component. Useful silicone-containing components preferably comprise polymerizable functional groups such as acrylate, methacrylate, acrylamide, methacrylamide, vinyl, N-vinyl lactam, N-vinylamide, and styryl functional groups.

In some examples, the ophthalmic lens skirt, also called an insert-encapsulating layer, that surrounds the insert may be comprised of standard hydrogel ophthalmic lens formulations. Exemplary materials with characteristics that may provide an acceptable match to numerous insert materials may include, the Narafilcon family (including Narafilcon A and Narafilcon B), and the Etafilcon family (including Etafilcon A). A more technically inclusive discussion follows on the nature of materials consistent with the art herein. One ordinarily skilled in the art may recognize that other material other than those discussed may also form an acceptable enclosure or partial enclosure of the sealed and encapsulated inserts and should be considered consistent and included within the scope of the claims.

Suitable silicone containing components include compounds of Formula I

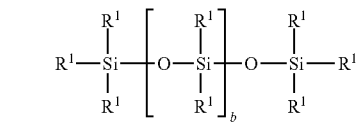

where $R^1$ is independently selected from monovalent reactive groups, monovalent alkyl groups, or monovalent aryl groups, any of the foregoing which may further comprise functionality selected from hydroxy, amino, oxa, carboxy, alkyl carboxy, alkoxy, amido, carbamate, carbonate, halogen or combinations thereof; and monovalent siloxane chains comprising 1-100 Si—O repeat units which may further comprise functionality selected from alkyl, hydroxy, amino, oxa, carboxy, alkyl carboxy, alkoxy, amido, carbamate, halogen or combinations thereof;

where b=0 to 500, where it is understood that when b is other than 0, b is a distribution having a mode equal to a stated value;

wherein at least one $R^1$ comprises a monovalent reactive group, and in some examples between one and 3 $R^1$ comprise monovalent reactive groups.

As used herein "monovalent reactive groups" are groups that may undergo free radical and/or cationic polymerization. Non-limiting examples of free radical reactive groups include (meth)acrylates, styryls, vinyls, vinyl ethers, $C_{1-6}$alkyl(meth)acrylates, (meth)acrylamides, $C_{1-6}$alkyl (meth)acrylamides, N-vinyllactams, N-vinylamides, $C_{2-12}$alkenyls, $C_{2-12}$alkenylphenyls, $C_{2-12}$alkenylnaphthyls, $C_{2-6}$alkenylphenyl$C_{1-6}$alkyls, O-vinylcarbamates and O-vinylcarbonates. Non-limiting examples of cationic reactive groups include vinyl ethers or epoxide groups and mixtures thereof. In one embodiment the free radical reactive groups comprises (meth)acrylate, acryloxy, (meth)acrylamide, and mixtures thereof.

Suitable monovalent alkyl and aryl groups include unsubstituted monovalent $C_1$ to $C_{16}$alkyl groups, $C_6$-$C_{14}$ aryl groups, such as substituted and unsubstituted methyl, ethyl, propyl, butyl, 2-hydroxypropyl, propoxypropyl, polyethyleneoxypropyl, combinations thereof and the like.

In one example, b is zero, one $R^1$ is a monovalent reactive group, and at least 3 $R^1$ are selected from monovalent alkyl groups having one to 16 carbon atoms, and in another example from monovalent alkyl groups having one to 6 carbon atoms. Non-limiting examples of silicone components of this embodiment include 2-methyl-,2-hydroxy-3-[3-[1,3,3,3-tetramethyl-1-[(trimethylsilyl)oxy]disiloxanyl] propoxy]propyl ester ("SiGMA"), 2-hydroxy-3-methacryloxypropyloxypropyl-tris (trimethylsiloxy)silane, 3-methacryloxypropyltris(trimethylsiloxy)silane ("TRIS"), 3-methacryloxypropylbis(trimethylsiloxy)methylsilane and 3-methacryloxypropylpentamethyl disiloxane.

In another example, b is 2 to 20, 3 to 15 or in some examples 3 to 10; at least one terminal $R^1$ comprises a monovalent reactive group and the remaining $R^1$ are selected from monovalent alkyl groups having 1 to 16 carbon atoms, and in another embodiment from monovalent alkyl groups having 1 to 6 carbon atoms. In yet another embodiment, b is 3 to 15, one terminal $R^1$ comprises a monovalent reactive group, the other terminal R¹ comprises a monovalent alkyl group having 1 to 6 carbon atoms and the remaining R¹ comprise monovalent alkyl group having 1 to 3 carbon atoms. Non-limiting examples of silicone components of this embodiment include (mono-(2-hydroxy-3-methacryloxypropyl)-propyl ether terminated polydimethylsiloxane (400-1000 MW)) ("OH-mPDMS"), monomethacryloxypropyl terminated mono-n-butyl terminated polydimethylsiloxanes (800-1000 MW), ("mPDMS").

In another example, b is 5 to 400 or from 10 to 300, both terminal R¹ comprise monovalent reactive groups and the remaining R¹ are independently selected from monovalent alkyl groups having 1 to 18 carbon atoms, which may have ether linkages between carbon atoms and may further comprise halogen.

In one example, where a silicone hydrogel lens is desired, the lens of the present invention will be made from a reactive mixture comprising at least about 20 and preferably between about 20 and 70% wt silicone containing components based on total weight of reactive monomer components from which the polymer is made.

In another embodiment, one to four R¹ comprises a vinyl carbonate or carbamate of the formula:

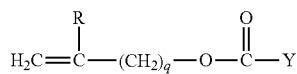

Formula II wherein: Y denotes O—, S— or NH—;
R denotes, hydrogen or methyl; d is 1, 2, 3 or 4; and q is 0 or 1.

The silicone-containing vinyl carbonate or vinyl carbamate monomers specifically include: 1,3-bis[4-(vinyloxycarbonyloxy)but-1-yl]tetramethyl-disiloxane; 3-(vinyloxycarbonylthio) propyl-[tris (trimethylsiloxy)silane]; 3-[tris (trimethylsiloxy)silyl] propyl allyl carbamate; 3-[tris (trimethylsiloxy)silyl] propyl vinyl carbamate; trimethylsilylethyl vinyl carbonate; trimethylsilylmethyl vinyl carbonate, and

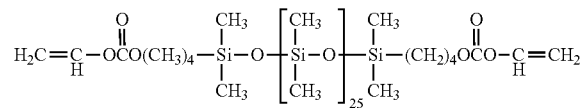

Where biomedical devices with modulus below about 200 are desired, only one R¹ shall comprise a monovalent reactive group and no more than two of the remaining R¹ groups will comprise monovalent siloxane groups.

Another class of silicone-containing components includes polyurethane macromers of the following formulae:

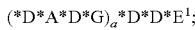
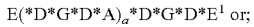
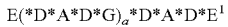

Formulae IV-VI wherein:
D denotes an alkyl diradical, an alkyl cycloalkyl diradical, a cycloalkyl diradical, an aryl diradical or an alkylaryl diradical having 6 to 30 carbon atoms,
G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;
* denotes a urethane or ureido linkage;
$a$ is at least 1;
A denotes a divalent polymeric radical of formula:

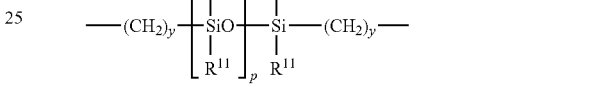

Formula VII $R^{11}$ independently denotes an alkyl or fluoro-substituted alkyl group having 1 to 10 carbon atoms, which may contain ether linkages between carbon atoms; y is at least 1; and p provides a moiety weight of 400 to 10,000; each of E and $E^1$ independently denotes a polymerizable unsaturated organic radical represented by formula:

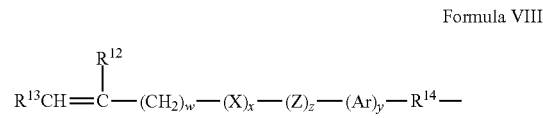

Formula VIII wherein: $R^{12}$ is hydrogen or methyl; $R^{13}$ is hydrogen, an alkyl radical having 1 to 6 carbon atoms, or a —CO—Y—$R^{15}$ radical wherein Y is —O—, Y—S— or —NH—; $R^{14}$ is a divalent radical having 1 to 12 carbon atoms; X denotes —CO— or —OCO—; Z denotes —O— or —NH—; Ar denotes an aromatic radical having 6 to 30 carbon atoms; w is 0 to 6; x is 0 or 1; y is 0 or 1; and z is 0 or 1.

A preferred silicone-containing component is a polyurethane macromer represented by the following formula:

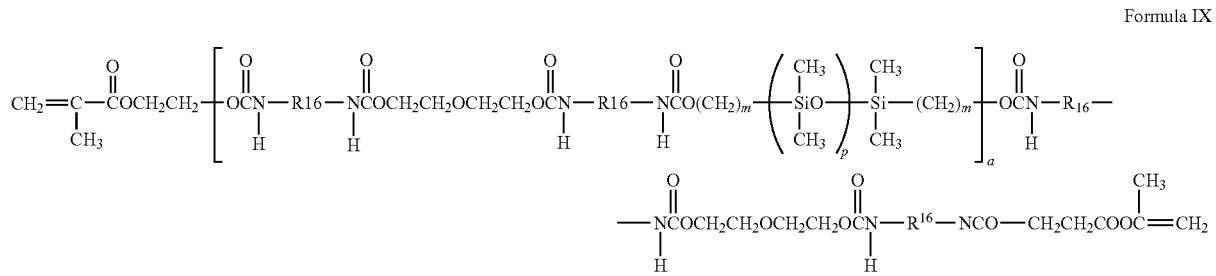

Formula IX wherein $R^{16}$ is a diradical of a diisocyanate after removal of the isocyanate group, such as the diradical of isophorone diisocyanate. Another suitable silicone containing macromer is compound of formula X (in which x+y is a number in the range of 10 to 30) formed by the reaction of fluoroether, hydroxy-terminated polydimethylsiloxane, isophorone diisocyanate and isocyanatoethylmethacrylate.

There may be other classes of liquid crystal materials that may be useful for the inventive concepts here. For example, ferroelectric liquid crystals may provide function for electric field oriented liquid crystal examples, but may also introduce other effects such as magnetic field interactions. Interactions of electromagnetic radiation with the materials may also differ.

Formula X

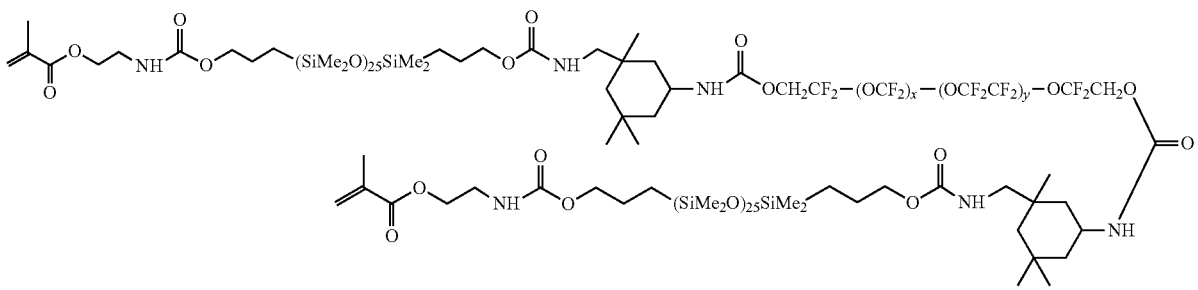

Other silicone containing components suitable for use in this invention include macromers containing polysiloxane, polyalkylene ether, diisocyanate, polyfluorinated hydrocarbon, polyfluorinated ether and polysaccharide groups; polysiloxanes with a polar fluorinated graft or side group having a hydrogen atom attached to a terminal difluoro-substituted carbon atom; hydrophilic siloxanyl methacrylates containing ether and siloxanyl linkanges and crosslinkable monomers containing polyether and polysiloxanyl groups. Any of the foregoing polysiloxanes may also be used as the silicone containing component in the present invention.

Liquid Crystal Materials

There may be numerous materials that may have characteristics consistent with the liquid crystal layer types that have been discussed herein. It may be expected that liquid crystal materials with favorable toxicity may be preferred and naturally derived cholesteryl based liquid crystal materials may be useful. In other examples, the encapsulation technology and materials of ophthalmic inserts may allow a broad choice of materials that may include the LCD display related materials which may typically be of the broad categories related to nematic or cholesteric N or smectic liquid crystals or liquid crystal mixtures. Commercially available mixtures such as Merck Specialty chemicals Licristal mixtures for TN, VA, PSVA, IPS and FFS applications and other commercially available mixtures may form a material choice to form a liquid crystal layer.

In a non-limiting sense, mixtures or formulations may comprise the following liquid crystal materials: 1-(trans-4-Hexylcyclohexyl)-4-isothiocyanatobenzene liquid crystal, benzoic acid compounds including (4-Octylbenzoic acid and 4-Hexylbenzoic acid), carbonitrile compounds including (4'-Pentyl-4-biphenylcarbonitrile, 4'-Octyl-4-biphenylcarbonitrile, 4'-(Octyloxy)-4-biphenylcarbonitrile, 4'-(Hexyloxy)-4-biphenylcarbonitrile, 4-(trans-4-Pentylcyclohexyl) benzonitrile, 4'-(Pentyloxy)-4-biphenylcarbonitrile, 4'-Hexyl-4-biphenylcarbonitrile), and 4,4'-Azoxyanisole.

In a non-limiting sense, formulations showing particularly high birefringence of $n_{par}-n_{pup}>0.3$ at room temperature may be used as a liquid crystal layer forming material. For example, such formulation referred to as W1825 may be as available from AWAT and BEAM Engineering for Advanced Measurements Co. (BEAMCO).

Alignment Layer Materials

In many of the examples that have been described, the liquid crystal layers within ophthalmic lenses may need to be aligned in various manners at insert boundaries. The alignment, for example, may be parallel or perpendicular to the boundaries of the inserts, and this alignment may be obtained by proper processing of the various surfaces. The processing may involve coating the substrates of the inserts that contain the liquid crystal (LC) by alignment layers. Those alignment layers are described herein.

A technique commonly practiced in liquid crystal based devices of various types may be the rubbing technique. This technique may be adapted to account for the curved surfaces such as the ones of the insert pieces used for enclosing the liquid crystal. In an example, the surfaces may be coated by a Polyvinyl Alcohol (PVA) layer. For example, a PVA layer may be spin coated using a 1 weight percent aqueous solution. The solution may be applied with spin coating at 1000 rpm for time such as approximately 60 s, and then dried. Subsequently, the dried layer may then be rubbed by a soft cloth. In a non-limiting example, the soft cloth may be velvet.

Photo-alignment may be another technique for producing alignment layers upon liquid crystal enclosures. In some examples, photo-alignment may be desirable due to its non-contact nature and the capability of large scale fabrication. In a non-limiting example, the photo-alignment layer used in the liquid crystal variable optic portion may be comprised of a dichroic azobenzene dye (azo dye) capable of aligning predominantly in the direction perpendicular to the polarization of linear polarized light of typically UV wavelengths. Such alignment may be a result of repetitive trans-cis-trans photoisomerization processes.

As an example, PAAD series azobenzene dyes may be spin coated from a 1 weight percent solution in DMF at 3000 rpm for 30 s. Subsequently, the obtained layer may be exposed to a linear polarized light beam of a UV wavelength (such as for example, 325 nm, 351 nm, 365 nm) or even a visible wavelength (400-500 nm). The source of the light may take various forms. In some examples, light may originate from laser sources for example. Other light sources such as LEDs, halogen and incandescent sources may be other non-limiting examples. Either before or after the various forms of light are polarized in the various patterns as appropriate, the light may be collimated in various manners such as through the use of optical lensing devices. Light from a laser source may inherently have a degree of collimation, for example.

A large variety of photoanisotropic materials are known currently, based on azobenzene polymers, polyesthers, photo-crosslinkable polymer liquid crystals with mesogenic 4-(4-methoxycinnamoyloxy)biphenyl side groups and the like. Examples of such materials include sulfonic bisazodye SD1 and other azobenzene dyes, particularly, PAAD-series materials available from BEAM Engineering for Advanced Measurements Co. (BEAMCO), Poly(vinyl cinnamates), and others.

In some examples, it may be desirable to use water or alcohol solutions of PAAD series azo dyes. Some azobenzene dyes, for example, Methyl Red, may be used for photoalignment by directly doping a liquid crystal layer. Exposure of the azobenzene dye to a polarized light may cause diffusion and adhesion of the azo dyes to and within the bulk of the liquid crystal layer to the boundary layers creating desired alignment conditions.

Azobenzene dyes such as Methyl Red may also be used in combination with a polymer, for example, PVA. Other photoanisotropic materials capable of enforcing alignment of adjacent layers of liquid crystals may be acceptable are known currently. These examples may include materials based on coumarines, polyesthers, photo-crosslinkable polymer liquid crystals with mesogenic 4-(4-methoxycinnamoyloxy)-biphenyl side groups, poly(vinyl cinnamates), and others. The photo-alignment technology may be advantageous for examples comprising patterned orientation of liquid crystal.

In another example of producing alignment layers, the alignment layer may be obtained by vacuum deposition of silicon oxide (SiOx where $1<=X<=2$) on the insert piece substrates. For example, $SiO_2$ may be deposited at low pressure such as $\sim 10^{-6}$ mbar. It may be possible to provide alignment features at a nanoscaled size that are injection molded into with the creation of the front and back insert pieces. These molded features may be coated in various manners with the materials that have been mentioned or other materials that may directly interact with physical alignment features and transmit the alignment patterning into alignment orientation of liquid crystal molecules.

Ion-beam alignment may be another technique for producing alignment layers upon liquid crystal enclosures. In some examples, a collimated argon ion or focused gallium ion beam may be bombarded upon the alignment layer at a defined angle/orientation. This type of alignment may also be used to align silicon oxide, diamond-like-carbon (DLC), polyimide and other alignment materials.

Still further examples may relate to the creation of physical alignment features to the insert pieces after they are formed. Rubbing techniques as are common in other Liquid Crystal based art may be performed upon the molded surfaces to create physical grooves. The surfaces may also be subjected to a post-molding embossing process to create small grooved features upon them. Still further examples may derive from the use of etching techniques which may involve optical patterning processes of various kinds.

Dielectric Materials

Dielectric films and dielectrics are described herein. By way of non-limiting examples, the dielectric film or dielectrics used in the liquid crystal variable optic portion possess characteristics appropriate to the invention described herein. A dielectric may comprise one or more material layers functioning alone or together as a dielectric. Multiple layers may be used to achieve dielectric performance superior to that of a single dielectric.

The dielectric may permit a defect-free insulating layer at a thickness desired for the discretely variable optic portion, for example, between 1 and 10 µm. A defect may be referred to as a pinhole, as is known by those skilled in the art to be a hole in the dielectric permitting electrical and/or chemical contact through the dielectric. The dielectric, at a given thickness, may meet requirements for breakdown voltage, for example, that the dielectric should withstand 100 volts or more.

The dielectric may allow for fabrication onto curved, conical, spherical, and complex three-dimensional surfaces (e.g., curved surfaces or non-planar surfaces). Typical methods of dip- and spin-coating may be used, or other methods may be employed.

The dielectric may resist damage from chemicals in the variable optic portion, for example the liquid crystal or liquid crystal mixture, solvents, acids, and bases or other materials that may be present in the formation of the liquid crystal region. The dielectric may resist damage from infrared, ultraviolet, and visible light. Undesirable damage may include degradation to parameters described herein, for example, breakdown voltage and optical transmission. The dielectric may resist permeation of ions. The dielectric may prevent electromigration, dendrite growth, and other degradations of the underlying electrodes. The dielectric may adhere to an underlying electrode and/or substrate, for example, with the use of an adhesion promotion layer. The dielectric may be fabricated using a process which allows for low contamination, low surface defects, conformal coating, and low surface roughness.

The dielectric may possess relative permittivity or a dielectric constant which is compatible with electrical operation of the system, for example, a low relative permittivity to reduce capacitance for a given electrode area. The dielectric may possess high resistivity, thereby permitting a very small current to flow even with high applied voltage. The dielectric may possess qualities desired for an optic device, for example, high transmission, low dispersion, and refractive index within a certain range. Example, non-limiting, dielectric materials, include one or more of Parylene-C, Parylene-HT, Silicon Dioxide, Silicon Nitride, and Teflon AF.

Electrode Materials

Electrodes are described herein for applying an electric potential for achieving an electric field across the liquid crystal region. An electrode generally comprises one or more material layers functioning alone or together as an electrode.

The electrode may adhere to an underlying substrate, dielectric coating, or other objects in the system, perhaps with the use of an adhesion promoter (e.g., methacryloxypropyltrimethoxysilane). The electrode may form a beneficial native oxide or be processed to create a beneficial oxide layer. The electrode may be transparent, substantially transparent or opaque, with high optical transmission and little reflection. The electrode may be patterned or etched with known processing methods. For example, the electrodes may be evaporated, sputtered, or electroplated, using photolithographic patterning and/or lift-off processes.

The electrode may be designed to have suitable resistivity for use in the electrical system described herein, for example, meeting the requirements for resistance in a given geometric construct.

The electrodes may be manufactured from one or more of indium tin oxide (ITO), aluminum-doped zinc oxide (AZO), gold, stainless steel, chrome, graphene, graphene-doped layers and aluminum. It will be appreciated that this is not an exhaustive list.

The electrodes may be used to establish an electric field in a region between the electrodes. In some examples, there may be numerous surfaces upon which electrodes may be formed. It may be possible to place electrodes on any or all of the surfaces that are defined, and an electric field may be established in the region between any of the surfaces upon which electrodes have been formed by application of electric potential to at least those two surfaces.

Processes

The following method steps are provided as examples of processes that may be implemented according to some aspects of the present invention. It should be understood that the order in which the method steps are presented is not meant to be limiting and other orders may be used to implement the invention. In addition, not all of the steps are required to implement the present invention and additional steps may be included in various examples of the present invention. It may be obvious to one skilled in the art that additional examples may be practical, and such methods are well within the scope of the claims.

Figure 7:
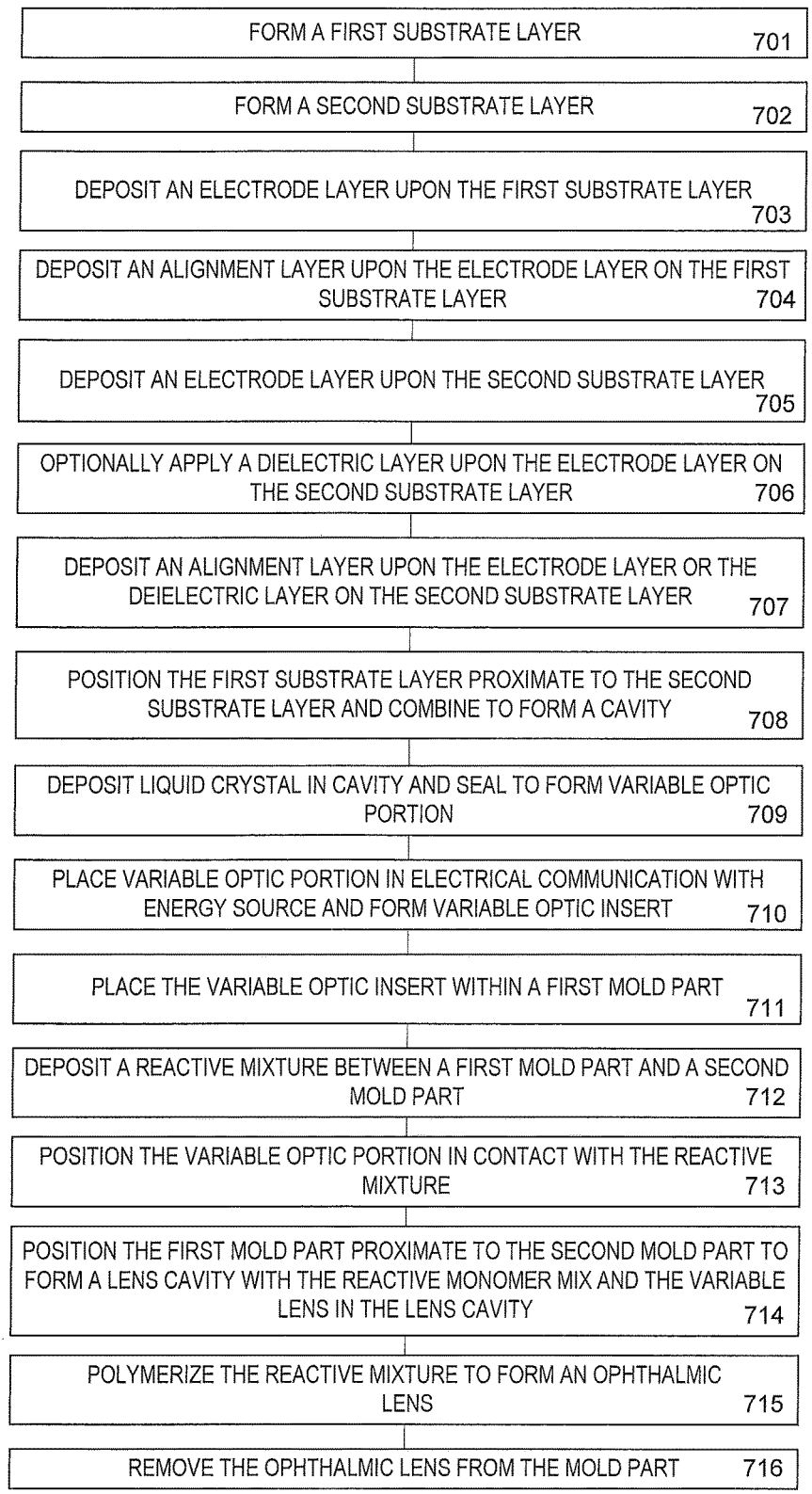
FIG. 7 illustrates method steps for forming an ophthalmic lens with a variable optic insert which may be comprised of cycloidally aligned regions of liquid crystal molecules between shaped insert pieces.

Referring to FIG. 7, a flowchart illustrates exemplary steps that may be used to implement the present invention. At 701, forming a first substrate layer which may comprise a back curve surface and have a top surface with a shape of a first type that may differ from the shape of surface of other substrate layers. In some examples, the difference may include a different radius of curvature of the surface at least in a portion that may reside in the optical zone. At 702, forming a second substrate layer which may comprise a front curve surface or an intermediate surface or a portion of an intermediate surface for more complicated devices. At 703, an electrode layer may be deposited upon the first substrate layer. The deposition may occur, for example, by vapor deposition or electroplating. In some examples, the first substrate layer may be part of an insert that has regions both in the optical zone and regions in the non-optic zone. The electrode deposition process may simultaneously define interconnect features in some embodiments. In some examples a dielectric layer may be formed upon the interconnects or electrodes. The dielectric layer may comprise numerous insulating and dielectric layers such as for example silicon dioxide.

At 704, the first substrate layer may be further processed to add an alignment layer upon the previously deposited dielectric or electrode layer. The alignment layers may be deposited upon the top layer on the substrate and then processed in standard manners, for example, rubbing techniques, to create the grooving features that are characteristic of standard alignment layers or by treatment with exposure to energetic particles or light. Thin layers of photoanisotropic materials may be processed with light exposure to form alignment layers with various characteristics. As mentioned previously, in methods to form layers of liquid crystal wherein polymer networked regions of interstitially located liquid crystal are formed, the methods may not include steps related to the formation of alignment layers.

At 705, the second substrate layer may be further processed. An electrode layer may be deposited upon the second substrate layer in an analogous fashion to step 703. Then in some examples, at 706, a dielectric layer may be applied upon the second substrate layer upon the electrode layer. The dielectric layer may be formed to have a variable thickness across its surface. As an example, the dielectric layer may be molded upon the first substrate layer. Alternatively, a previously formed dielectric layer may be adhered upon the electrode surface of the second substrate piece.

At 707, an alignment layer may be formed upon the second substrate layer in similar fashion to the processing step at 704. After 707, two separate substrate layers that may form at least a portion of an ophthalmic lens insert may be ready to be joined. In some examples at 708, the two pieces will be brought in close proximity to each other and then liquid crystal material may be filled in between the pieces. There may be numerous manners to fill the liquid crystal in between the pieces including as non-limiting examples, vacuum based filling where the cavity is evacuated and liquid crystal material is subsequently allowed to flow into the evacuated space. In addition, the capillary forces that are present in the space between the lens insert pieces may aid in the filling of the space with liquid crystal material. At 709, the two pieces may be brought adjacent to each other and then sealed to form a variable optic element with liquid crystal. There may be numerous manners of sealing the pieces together including the use of adhesives, sealants, and physical sealing components such as o-rings and snap lock features as non-limiting examples.

In some examples, two pieces of the type formed at 709 may be created by repeating method steps 701 to 709 wherein the alignment layers are offset from each other to allow for a lens that may adjust the focal power of non-polarized light. In such examples, the two variable optic layers may be combined to form a single variable optic insert. At 710, the variable optic portion may be connected to the energy source and intermediate or attached components may be placed thereon.

At 711, the variable optic insert resulting at step 710 may be placed within a mold part. The variable optic insert may or may not also comprise one or more components. In some preferred examples, the variable optic insert is placed in the mold part via mechanical placement. Mechanical placement may include, for example, a robot or other automation, such as that known in the industry to place surface-mount components. Human placement of a variable optic insert is also within the scope of the present invention. Accordingly, any mechanical placement or automation may be utilized which is effective to place a variable optic insert with an energy source within a cast mold part such that the polymerization of a reactive mixture contained by the mold part will include the variable optic in a resultant ophthalmic lens.

In some examples, a variable optic insert may be placed in a mold part attached to a substrate. An energy source and one or more components may also be attached to the substrate and may be in electrical communication with the variable optic insert. Components may include for example, circuitry to control power applied to the variable optic insert. Accordingly, in some examples a component includes control mechanism for actuating the variable optic insert to change one or more optical characteristics, such as, for example, a change of state between a first optical power and a second optical power.

In some examples, a processor device, microelectromechanical system (MEMS), nanoelectromechanical system (NEMS) or other component may also be placed into the variable optic insert and in electrical contact with the energy source. At 712, a reactive monomer mixture may be deposited into a mold part. At 713, the variable optic insert may be positioned into contact with the reactive mixture. In some examples the order of placement of variable optic and depositing of monomer mixture may be reversed. At 714, the first mold part is placed proximate to a second mold part to form a lens-forming cavity with at least some of the reactive monomer mixture and the variable optic insert in the cavity. As discussed above, preferred examples include an energy source and one or more components also within the cavity and in electrical communication with the variable optic insert.

At 715, the reactive monomer mixture within the cavity is polymerized. Polymerization may be accomplished, for example, via exposure to one or both of actinic radiation and heat. At 716, the ophthalmic lens is removed from the mold parts with the variable optic insert adhered to or encapsulated within the insert-encapsulating polymerized material making up the ophthalmic lens.

Although the invention herein may be used to provide hard or soft contact lenses made of any known lens material, or material suitable for manufacturing such lenses, preferably, the lenses of the invention are soft contact lenses having water contents of about 0 to about 90 percent. More preferably, the lenses are made of monomers containing hydroxy groups, carboxyl groups, or both or be made from silicone-containing polymers, such as siloxanes, hydrogels, silicone hydrogels, and combinations thereof. Material useful for forming the lenses of the invention may be made by reacting blends of macromers, monomers, and combinations thereof along with additives such as polymerization initiators. Suitable materials include, without limitation, silicone hydrogels made from silicone macromers and hydrophilic monomers.

Apparatus

Figure 8:
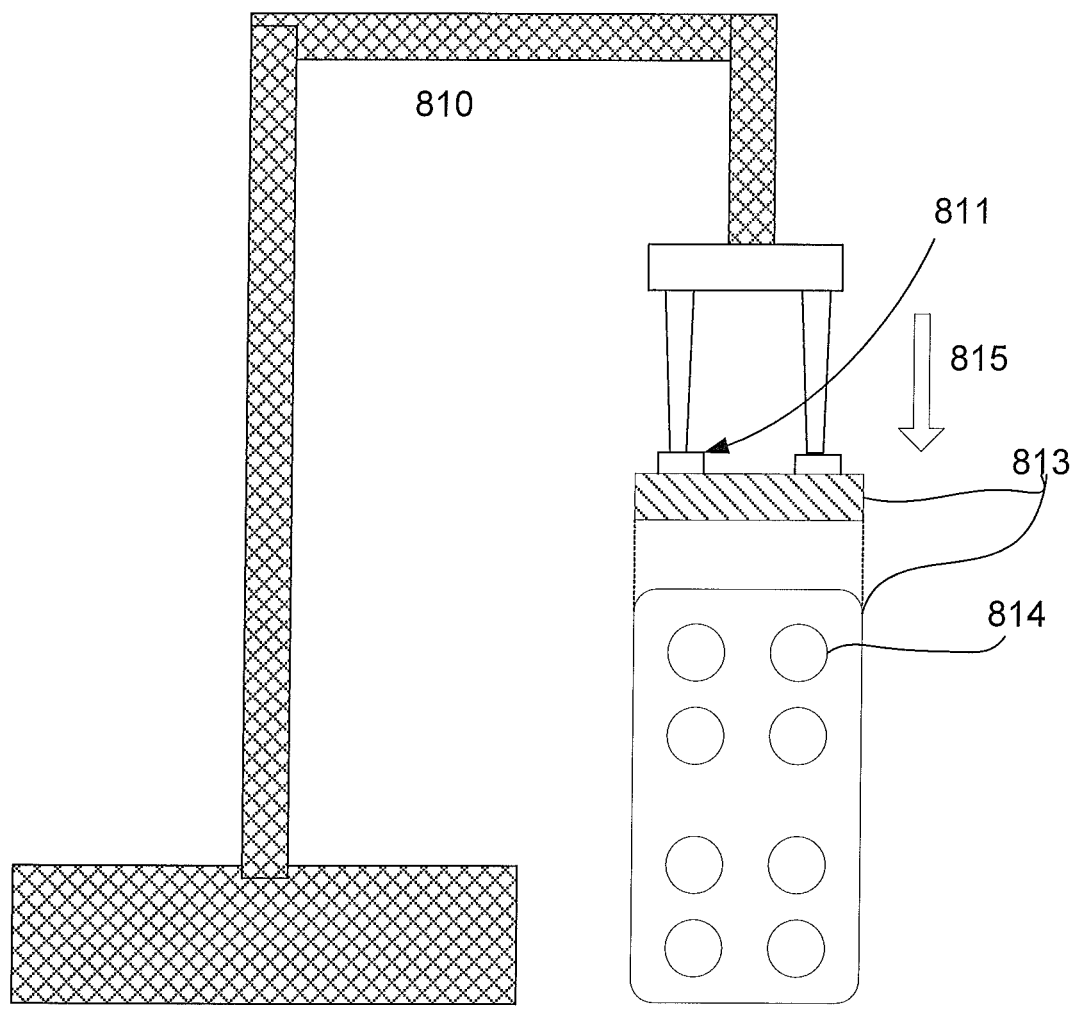
FIG. 8 illustrates an example of apparatus components for placing a variable optic insert comprised of cycloidally aligned regions of liquid crystal molecules between shaped insert pieces into an ophthalmic lens mold part.

Referring now to FIG. 8, automated apparatus 810 is illustrated with one or more transfer interfaces 811. Multiple mold parts, each with an associated variable optic insert 814 are contained on a pallet 813 and presented to transfer interfaces 811. Examples, may include, for example a single interface individually placing variable optic insert 814, or multiple interfaces (not shown) simultaneously placing variable optic inserts 814 into the multiple mold parts, and in some examples, in each mold part. Placement may occur via vertical movement 815 of the transfer interfaces 811.

Another aspect of some examples of the present invention includes apparatus to support the variable optic insert 814 while the body of the ophthalmic lens is molded around these components. In some examples the variable optic insert 814 and an energy source may be affixed to holding points in a lens mold (not illustrated). The holding points may be affixed with polymerized material of the same type that will be formed into the lens body. Other examples include a layer of prepolymer within the mold part onto which the variable optic insert 814 and an energy source may be affixed.

Processors Included in Insert Devices

Figure 9:
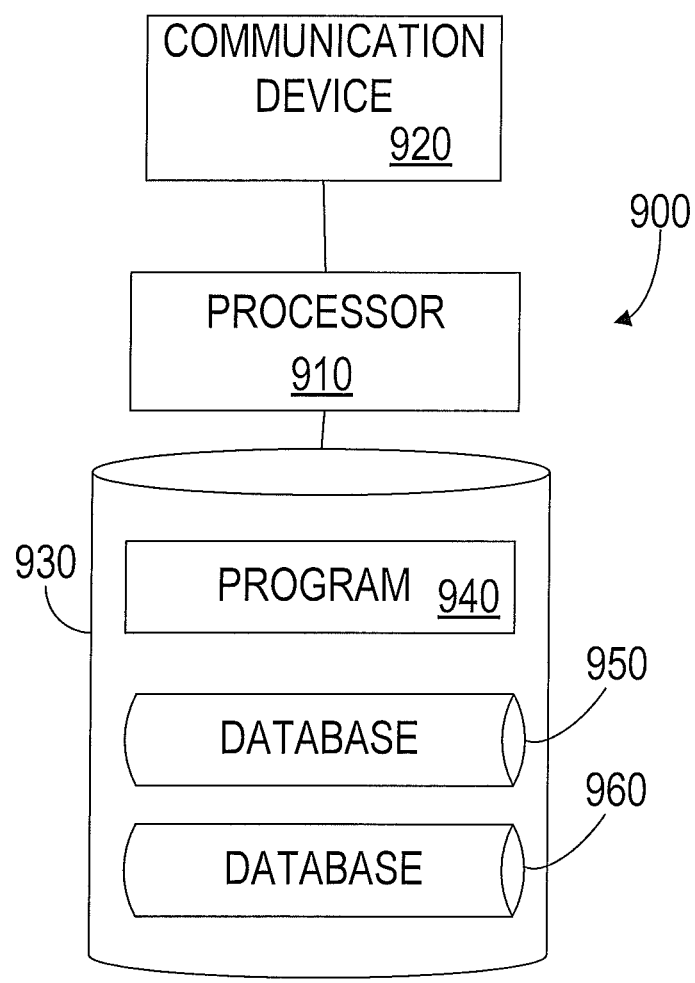
FIG. 9 illustrates a processor that may be used to implement some examples of the present invention.

Referring now to FIG. 9, a controller 900 is illustrated that may be used in some examples of the present invention. The controller 900 includes a processor 910, which may include one or more processor components coupled to a communication device 920. In some examples, a controller 900 may be used to transmit energy to the energy source placed in the ophthalmic lens.

The controller may include one or more processors, coupled to a communication device configured to communicate energy via a communication channel. The communication device may be used to electronically control one or more of the placement of a variable optic insert into the ophthalmic lens or the transfer of a command to operate a variable optic device.

The communication device 920 may also be used to communicate, for example, with one or more controller apparatus or manufacturing equipment components.

The processor 910 is also in communication with a storage device 930. The storage device 930 may comprise any appropriate information storage device, including combinations of magnetic storage devices (e.g., magnetic tape and hard disk drives), optical storage devices, and/or semiconductor memory devices such as Random Access Memory (RAM) devices and Read Only Memory (ROM) devices.

The storage device 930 may store a program 940 for controlling the processor 910. The processor 910 performs instructions of the program 940, and thereby operates in accordance with the present invention. For example, the processor 910 may receive information descriptive of variable optic insert placement, processing device placement, and the like. The storage device 930 may also store ophthalmic related data in one or more databases 950, 960. The database 950 and 960 may include specific control logic for controlling energy to and from a variable optic lens.

Intraocular Lenses

Figure 10:
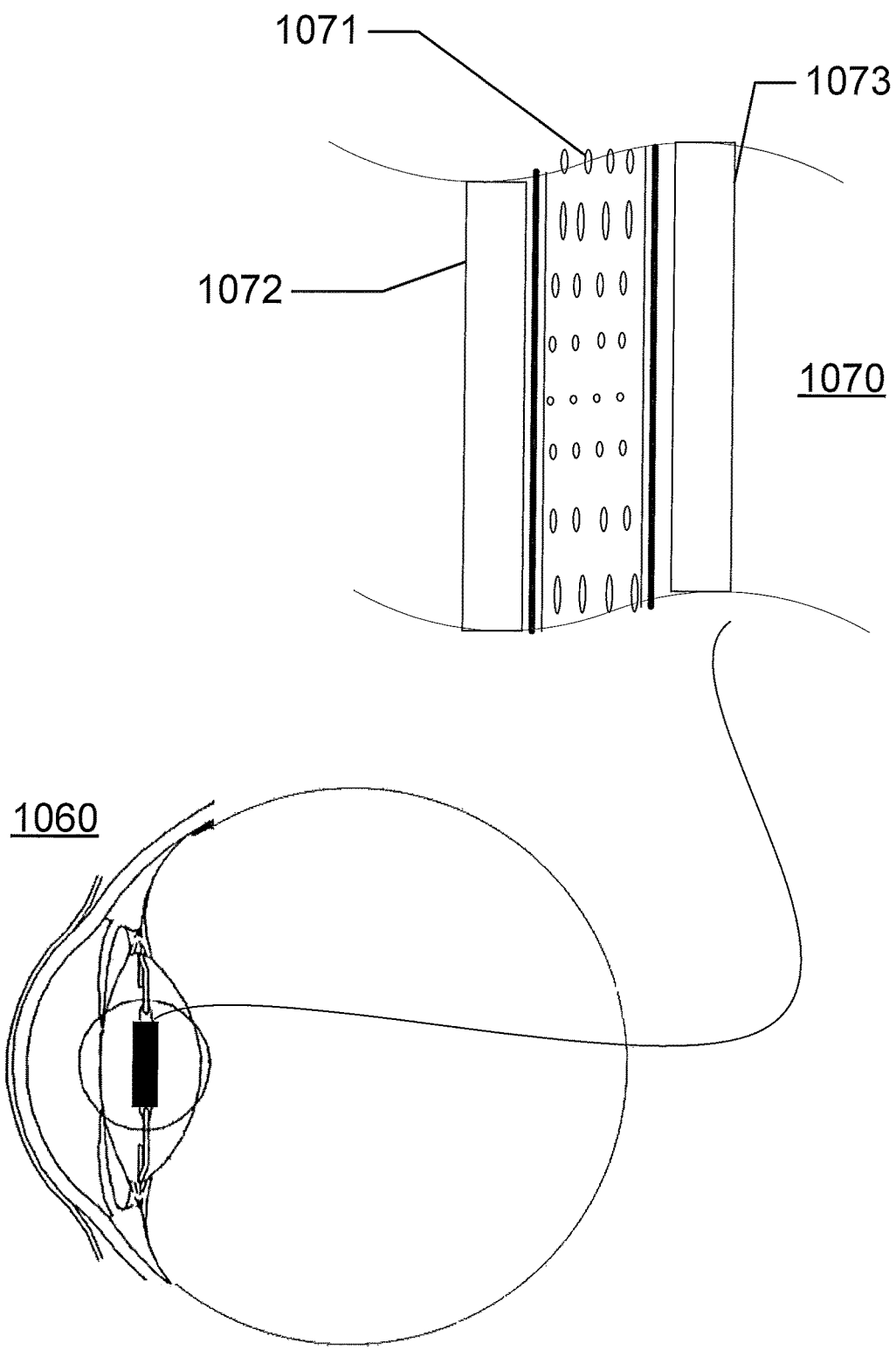
FIG. 10 illustrates a cross sectional view of an ophthalmic lens device embodiment with a variable optic insert wherein the variable optic portion may be comprised of cycloidally oriented liquid crystal.

Referring to FIG. 10, an intraocular device 1060 is shown in reference to an exemplary eye in cross section. An inset 1070 depicts a region of the intraocular device comprising liquid crystal material 1071. A first substrate 1072 and a second substrate 1073 may be coated with various layers as discussed herein including electrodes, dielectrics and alignment layers. Portions of the intraocular device 1070 may overlap with the optical zone of the lens 1060. The first substrate 1072 and the second substrate 1073 are shown in an exemplary sense as flat surfaces, however in some examples they may assume a curved shape as well. The liquid crystal material 1071 is illustrated in such a manner to reflect a local region of liquid crystal material oriented in a cycloidal pattern according to the current disclosure.

In this description, reference has been made to elements illustrated in the figures. Many of the elements are depicted for reference to depict the examples of the inventive art for understanding. The relative scale of actual features may be significantly different from that as depicted, and variation from the depicted relative scales should be assumed within the spirit of the art herein. For example, liquid crystal molecules may be of a scale to be impossibly small to depict against the scale of insert pieces. The depiction of features that represent liquid crystal molecules at a similar scale to insert pieces to allow for representation of factors such as the alignment of the molecules is therefore such an example of a depicted scale that in actual examples may assume much different relative scale.

Although shown and described in what is believed to be the most practical and preferred examples, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An intraocular lens device with a variable optic insert positioned within at least a portion of an optical zone of the intraocular lens device, wherein the variable optic insert comprises:
   a curved first front surface and a curved first back surface wherein the first front surface and the first back surface are configured to form at least a first chamber;
   a first layer of electrode material proximate to the curved first front surface;
   a second layer of electrode material proximate to the curved first back surface;

a first layer containing liquid crystal material positioned within the first chamber, wherein the layer includes regions of liquid crystal material aligned in a pattern across at least a first portion of the variable optic insert that varies with a cycloidal pattern, and wherein the first layer containing liquid crystal material varies its first index of refraction affecting a ray of light traversing the first layer containing liquid crystal material when an electric potential is applied across the first layer of electrode material and the second layer of electrode material;

a curved second front surface and a curved second back surface wherein the second front surface and the second back surface are configured to form at least a second chamber;

a third layer of electrode material proximate to the curved second front surface;

a fourth layer of electrode material proximate to the curved second back surface;

a second layer containing liquid crystal material positioned within the second chamber, wherein the second layer filters out a circular polarization component of incident light;

an energy source embedded in the insert in at least a region comprising a non-optical zone; and an electrical circuit comprising a processor, wherein the electrical circuit controls a flow of electrical energy from the energy source to one or more of the first, second, third or fourth electrode layers; and wherein the variable optic insert alters a focal characteristic of the intraocular lens device.

* * * * *